United States Patent
Belanoff et al.

(10) Patent No.: US 11,268,145 B2
(45) Date of Patent: *Mar. 8, 2022

(54) METHODS FOR TREATING CUSHING'S SYNDROME

(71) Applicant: Corcept Therapeutics, Inc., Menlo Park, CA (US)

(72) Inventors: Joseph K. Belanoff, Menlo Park, CA (US); Hazel Hunt, West Sussex (GB); John Francis Unitt, Nottingham (GB); Andreas G. Moraitis, Menlo Park, CA (US)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,666

(22) Filed: Dec. 12, 2017

(65) Prior Publication Data

US 2018/0100179 A1    Apr. 12, 2018

Related U.S. Application Data

(63) Continuation of application No. 15/570,710, filed as application No. PCT/US2016/033143 on May 18, 2016, now Pat. No. 10,604,807.

(60) Provisional application No. 62/163,130, filed on May 18, 2015.

(51) Int. Cl.

| | |
|---|---|
| *A61K 31/567* | (2006.01) |
| *C12Q 1/6883* | (2018.01) |
| *A61K 31/573* | (2006.01) |
| *A61K 45/06* | (2006.01) |
| *G01N 33/573* | (2006.01) |
| *C12Q 1/533* | (2006.01) |
| *A61P 5/46* | (2006.01) |
| *A61K 31/4745* | (2006.01) |
| *G01N 33/74* | (2006.01) |

(52) U.S. Cl.
CPC ........ *C12Q 1/6883* (2013.01); *A61K 31/4745* (2013.01); *A61K 31/567* (2013.01); *A61K 31/573* (2013.01); *A61K 45/06* (2013.01); *A61P 5/46* (2018.01); *C12Q 1/533* (2013.01); *C12Y 502/01008* (2013.01); *G01N 33/573* (2013.01); *G01N 33/743* (2013.01); *C12Q 2600/106* (2013.01); *C12Q 2600/158* (2013.01); *G01N 2333/723* (2013.01); *G01N 2333/99* (2013.01); *G01N 2800/04* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2008/0118521 | A1 | 5/2008 | Spring et al. |
| 2012/0039812 | A1 | 2/2012 | Holsboer et al. |
| 2012/0094945 | A1 | 4/2012 | Diamond et al. |
| 2014/0170768 | A1 | 6/2014 | Ehrenkranz |

FOREIGN PATENT DOCUMENTS

| | | |
|---|---|---|
| JP | 2009132743 A | 6/2009 |
| JP | 2013090761 A | 5/2013 |
| WO | 0244418 A2 | 6/2002 |
| WO | 2013039916 A1 | 3/2013 |
| WO | 2013/177559 A2 | 11/2013 |

OTHER PUBLICATIONS

Chu et al (J Clinical Endocrinol and Metab 86:3568-3573, 2001) (Year: 2001).*
Vermeer et al (J Clinical Endocrinol and Metab 88:277-284, 2003) (Year: 2003).*
Vilar et al (Arq Bras Endocrinol Metab 51:1207-1216, 2007) (Year: 2007).*
Glaxosmithkline, "A Randomized, Double Blind, Placebo Controlled, 4 Period, Incomplete Block, Crossover Study Assessing the Dose-response Curve of Fluticasone Propionate in an Antigen Challenge Chamber", Clinical Trials, Aug. 23, 2012, pp. 1-5 <https://clinicaltrials.gov/ct2/show/NCT00848965>.
Lee et al., "A measure of glucocorticoid load provided by DNA methylation of Fkbp5 in mice", Psychopharmacology (2011) 218:303-312.
PCT/US2016/033143, "International Search Report and Written Opinion", dated Oct. 5, 2016, pp. 1-15.
EP16797242.1 , "Partial Supplementary European Search Report", dated Apr. 17, 2019, 10 pages.
U.S. Appl. No. 15/570,710 , "Final Office Action," dated Jun. 26, 2019, 11 pages.
EP16797242.1, "Extended European Search Report," dated Jun. 5, 2019, 16 pages.
Lee et al., "Chronic Corticosterone Exposure Increases Expression and Decreases Deoxyribonucleic Acid Methylation of Fkbp5 in Mice," Endocrinology, vol. 151, No. 9, Sep. 1, 2010, pp. 4332-4343.
JP2017-559803 , "Office Action", dated Nov. 28, 2019, 14 pages.
Application No. AU2016264321 , "First Examination Report", dated May 22, 2020, 6 pages.
Application No. JP2017-559803 , "Office Action", dated Apr. 20, 2020, 6 pages.
Application No. JP2017-559803 , Notice of Allowance, dated Aug. 19, 2020, 3 pages.
Application No. PH1-2017-502099 , Substantive Examination Report, dated Jun. 2, 2020, 3 pages.
Sabbagh et al., "Age-Associated Epigenetic Upregulation of the FKBP5 Gene Selectively Impairs Stress Resiliency",PLoS ONE, vol. 9, No. 9, Sep. 5, 2014, 8 pages, e107241, XP55590373,DOI: 10.1371 /journal.pone.0107241.

(Continued)

*Primary Examiner* — Craig D Ricci
(74) *Attorney, Agent, or Firm* — Kilpatrick Townsend & Stockton LLP

(57) ABSTRACT

Methods are provided for assessing a clinical response to a glucocorticoid receptor antagonist (GRA) in a human subject and for diagnosing Cushing's syndrome.

2 Claims, 2 Drawing Sheets

(56) References Cited

OTHER PUBLICATIONS

AU2016264321, "Second Examination Report", dated Aug. 26, 2020, 5 pages.

* cited by examiner

METHODS FOR TREATING CUSHING'S SYNDROME

CROSS-REFERENCES TO RELATED APPLICATIONS

This application is a continuation of U.S. patent application Ser. No. 15/570,710, filed Oct. 30, 2017, which is a U.S. National Stage Entry application under 35 U.S.C. § 371 of International Application PCT/US2016/033143, filed May 18, 2016, which claims priority to U.S. Provisional Application Ser. No. 62/163,130, filed on May 18, 2015, the contents of all of which applications are hereby incorporated in their entirety for all purposes.

BACKGROUND OF THE INVENTION

Glucocorticoids (GCs) are a class of steroid hormones that bind to and activate the glucocorticoid receptor (GR), which is present in almost every vertebrate cell. The GR is pleiotropic and regulates a variety of important pathways in the vertebrate organism, for example, metabolism, immunity, and development. As such, detection of GR activity or regulation can be used to diagnose a variety of different vertebrate diseases, or assess a clinical or biochemical response to treatments that modulate GR activity.

For example, detection of GR activity or regulation can be used for detection of various forms of Cushing's syndrome. As another example, glucocorticoid receptor antagonists (GRAs) can be administered to a patient to treat a number of different diseases and conditions, and detection of a change in GR activity in response to administration of the GRA can indicate or assess a clinical or biochemical response to the treatment. However, current methods and compositions for assessing GR activity suffer from one or more of the following insufficiencies: high cost, low sensitivity, low specificity, high false positive rate, or high false negative rate. Therefore, there remains a need for improved methods and compositions for detection of GR activity.

BRIEF SUMMARY OF THE INVENTION

In a first aspect, the present invention provides a method for assessing a clinical or biochemical response to a glucocorticoid receptor antagonist (GRA) in a human subject, the method comprising: a) measuring a first amount, or activity of 51 kDa FK506 binding protein (FKBP5 protein) or a first expression level of a gene encoding FKBP5 protein in a first sample from the subject, wherein: i) the first sample comprises primary cells; and ii) the first sample is or was obtained before administering the GRA to the subject; b) optionally administering the GRA to the subject; c) measuring a second amount or activity of FKBP5 protein or a second expression level of a gene encoding FKBP5 protein in a second sample from the subject, wherein: i) the second sample comprises primary cells; and ii) the second sample is or was obtained after administering the GRA to the subject; and d) comparing the first and second amounts, activities, or expression levels, wherein a reduction in the amount or activity of FKBP5 protein or a reduction in the expression level of the gene encoding FKBP5 protein in the second sample as compared to the first sample indicates the clinical or biochemical response to the GRA. In some cases, the absence of a reduction indicates a lack of a clinical response or a lack of biochemical response to the GRA.

In a second aspect, the present invention provides a method for assessing a clinical or biochemical response to a GRA in a human subject, the method comprising: a) measuring a first amount, or activity of 51 kDa FK506 binding protein (FKBP5 protein) or a first expression level of a gene encoding FKBP5 protein in a first sample from the subject, wherein: i) the first sample comprises primary cells; and ii) the first sample is or was obtained before administering the GRA to the subject; b) optionally administering the GRA to the subject; c) measuring a second amount or activity of FKBP5 protein or a second expression level of a gene encoding FKBP5 protein in a second sample from the subject, wherein: i) the second sample comprises primary cells; and ii) the second sample is or was obtained after administering the GRA to the subject; d) comparing the first and second amounts, activities, or expression levels to obtain an FKBP5 difference value; e) comparing the difference value to a threshold difference value derived from a cohort of at least 20 or 30 or 50 test individuals; and f) identifying the subject as having or not having the clinical or biochemical response to the GRA based on a comparison of the difference value and threshold difference value. In some cases, the threshold difference value is a threshold reduction value and a presence of a reduction in FKBP5 amount or activity between the first and second sample that is greater than a threshold reduction value indicates a clinical or biochemical response to the GRA. In some cases, the threshold difference value is a threshold reduction value and a presence of a reduction in FKBP5 amount or activity between the first and second sample that is similar to (e.g., within about 5%, 10%, 15%, 20%, 25%, 30%, 35%, 40%, 45%, 50%, 60%, or 70% of) a threshold reduction value indicates a clinical or biochemical response to the GRA. In some cases, the at least 20 or 30 or 50 test individuals are subjects known to have or suspected of having Cushing's syndrome. In some cases, the threshold difference value is determined by subtracting a post-GRA administration FKBP5 amount, activity, or expression from a pre-GRA administration FKBP5 amount, activity, or expression in a cohort of 20 or 30 or 50 test individuals known to have or suspected of having Cushing's syndrome that is controlled or well-controlled by GRA administration.

In some embodiments, the subject is administered a GRA in multiple doses and the first sample is obtained prior to administering the multiple doses of GRA and the second sample is obtained after administering the multiple doses of GRA to the subject. In some embodiments the measuring of a) and/or c) comprises quantitating an amount of mRNA encoding FKBP5 protein in the sample. In some embodiments, the measuring of a) and/or c) comprises quantitating the amount of FKBP5 protein in the sample. In some embodiments the measuring comprises quantitating the amount of FKBP5 protein activity in the sample. In some embodiments, the quantitating the amount of FKBP5 protein activity in the sample comprises measuring FKBP5 protein peptidyl-prolyl-cis-trans isomerase activity in the sample. In some embodiments, the quantitating the amount of FKBP5 protein activity in the sample comprises measuring the amount of FKBP5 protein bound to glucocorticoid receptor (GR) in the sample.

In some embodiments, the administering the GRA to the subject comprises administering mifepristone to the subject. In some embodiments, the administering the GRA to the subject comprises administering a GRA that is not mifepristone to the subject. In some embodiments, the administering the GRA to the subject comprises administering a heteroaryl-ketone GRA. In some embodiments, the first or second samples comprise whole blood, or a fraction thereof. In some embodiments, the first and second samples comprise whole blood, or a fraction thereof. In some embodiments, the first or second samples comprise nasal epithelial scraping samples. In some embodiments, the patient is in need of administration of the glucocorticoid receptor antagonist (GRA). In some embodiments, the patient has elevated levels of cortisol.

In some embodiments, the patient has cancer and the first and second samples comprise tumor cells. In some embodiments, the first or second samples comprise whole blood, or a fraction thereof. In some embodiments, the first and second samples comprise whole blood, or a fraction thereof. In some embodiments, the method comprises administering an increased amount of GRA to the subject in the absence of a detected reduction in the amount or activity of FKBP5 protein or a detected reduction in the expression level of the gene encoding FKBP5 protein in the second sample.

In a third aspect, the present invention provides a method for diagnosing Cushing's syndrome in a human subject, the method comprising: a) measuring an amount, or activity of 51 kDa FK506 binding protein (FKBP5 protein) or an expression level of a gene encoding FKBP5 protein in a sample obtained or provided from the subject, wherein the sample comprises primary cells; and b) identifying the subject as likely to be suffering from Cushing's syndrome when the amount, activity or expression level is high relative to a control. In some cases, the control comprises a value derived from at least 100 or at least 200 test individuals. In some cases, the test individuals are subjects that are known to not exhibit Cushing's syndrome. In some cases, the test individuals are subjects that are known to have normal cortisol levels or are known to lack hypercortisolemia. In some cases, the control comprises a value derived from at least 20 or 30 or 50 test individuals. In some cases, the test individuals are subjects diagnosed with Cushing's syndrome and undergoing therapy with a GRA. In some cases, the test individuals are subjects diagnosed with Cushing's syndrome, undergoing therapy with a GRA, wherein at least one symptom of the Cushing's syndrome is mitigated or eliminated by the GRA therapy.

In a fourth aspect, the present invention provides a method for assessing a clinical or biochemical response to a GRA in a human subject, the method comprising: a) measuring an amount, or activity of 51 kDa FK506 binding protein (FKBP5 protein) or an expression level of a gene encoding FKBP5 protein in a sample from the subject, wherein: i) the sample comprises primary cells; and ii) the sample is or was obtained after administering the GRA to the subject; d) comparing the amount, activities, or expression level of FKBP5 to a control value derived from a cohort of at least 100 or at least 200 test individuals; and f) identifying the subject as having or not having the clinical or biochemical response to the GRA based on a comparison of the FKBP5 amount, activity or expression level to the control value. In some cases, the at least 100 or at least 200 test individuals are normal subjects that are not otherwise in need of a GRA. In some cases, the at least 100 or at least 200 test individuals do not have Cushing's syndrome. In some cases, the at least 100 or at least 200 test individuals do not have elevated levels of cortisol. In some cases, the at least 100 or at least 200 test individuals do not have, or do not exhibit symptoms of hypercortisolemia.

In some embodiments, the measuring comprises quantitating an amount of mRNA encoding FKBP5 protein in the primary cells of the sample. In some embodiments, the measuring comprises quantitating the amount of FKBP5 protein in the primary cells of the sample. In some embodiments, the measuring comprises quantitating the amount of FKBP5 protein activity in the primary cells of the sample. In some embodiments, the quantitating the amount of FKBP5 protein activity in the primary cells of the sample comprises quantitating FKBP5 protein peptidyl-prolyl-cis-trans isomerase activity in the primary cells of the sample. In some embodiments, the quantitating the amount of FKBP5 protein activity in the primary cells of the sample comprises quantitating the amount of FKBP5 protein bound to GR in the primary cells of the sample. In some embodiments, the sample obtained from the subject comprises whole blood, or a fraction thereof. In some embodiments, the subject has undergone transsphenoidal surgery before the sample is obtained from the subject. In some embodiments, the sample is obtained from the subject less than eleven days after the subject is treated with transsphenoidal surgery. In some embodiments, the sample is obtained from the subject less than two, four, or six weeks after the subject is treated with transsphenoidal surgery. In some embodiments, the method comprises administering a treatment for Cushing's syndrome when the amount or activity of FKBP5 protein or the expression level of the gene encoding FKBP5 protein is high relative to a control. In some cases, the administering the treatment for Cushing's syndrome comprises administering to the subject a glucocorticoid receptor antagonist (GRA)

In a fifth aspect, the present invention provides a method for assessing a clinical or biochemical response in a human subject to administering to the subject a medical or surgical therapy for treatment of hypercortisolemia, the method comprising: a) measuring a first amount, or activity of 51 kDa FK506 binding protein (FKBP5 protein) or a first expression level of a gene encoding FKBP5 protein in a first sample from the subject, wherein: i) the first sample comprises primary cells; and ii) the first sample is or was obtained before administering the medical or surgical therapy for treatment of hypercortisolemia to the subject; b) optionally administering the medical or surgical therapy for treatment of hypercortisolemia to the subject; c) measuring a second amount or activity of FKBP5 protein or a second expression level of a gene encoding FKBP5 protein in a second sample from the subject, wherein: i) the second sample comprises primary cells; and ii) the second sample is or was obtained after administering the medical or surgical therapy for treatment of hypercortisolemia to the subject; and d) comparing the first and second amounts, activities, or expression levels, wherein a reduction in the amount or activity of FKBP5 protein or a reduction in the expression level of the gene encoding FKBP5 protein in the second sample indicates the clinical response or the biochemical response to the medical or surgical therapy for treatment of hypercortisolemia. For example, a reduction in the amount or activity of FKBP5 protein or a reduction in the expression level of the gene encoding FKBP5 protein in the second sample can indicate that the medical or surgical therapy is successful in treating the hypercortisolism.

In a sixth aspect, the present invention provides a method for assessing a clinical or biochemical response to administering to the subject a medical or surgical therapy for treatment of hypercortisolemia, the method comprising: a) measuring a first amount, or activity of 51 kDa FK506 binding protein (FKBP5 protein) or a first expression level of a gene encoding FKBP5 protein in a first sample from the subject, wherein: i) the first sample comprises primary cells; and ii) the first sample is or was obtained before administering the GRA to the subject; b) optionally administering the medical or surgical therapy for treatment of hypercortisolemia to the subject; c) measuring a second amount or activity of FKBP5 protein or a second expression level of a gene encoding FKBP5 protein in a second sample from the subject, wherein: i) the second sample comprises primary cells; and ii) the second sample is or was obtained after administering the GRA to the subject; d) comparing the first and second amounts, activities, or expression levels to obtain an FKBP5 difference value; e) comparing the difference value to a threshold difference value derived from a cohort of at least 20 or 30 or 50 test individuals; and f) identifying the subject as having or not having the clinical or biochemical response to the GRA based on a comparison of the difference value and threshold difference value. In some cases, the threshold difference value is a threshold reduction value and a presence of a reduction in FKBP5 amount or activity between the first and second sample that is greater than, or similar to, a threshold reduction value indicates a clinical or biochemical response to the GRA. In some cases, the at least 20 or 30 or 50 test individuals are subjects known to have or suspected of having Cushing's syndrome.

In some embodiments, the medical or surgical therapy for treatment of hypercortisolemia is selected from the group consisting of: inhibition of steroidogenesis, administration of an ACTH modulator, GRA administration, transsphenoidal surgery, repeat transsphenoidal surgery, unilateral adrenalectomy, bilateral adrenalectomy, radiotherapy, resection of a non-pituitary ACTH-secreting tumor, treatment with a peptide receptor radionuclide therapy, and combinations thereof. In some embodiments, the inhibition of steroidogenesis comprises administration of ketoconazole, levoketoconazole, metyrapone, LCI699, mitotane, aminoglutethimide, etomidate, or a combination thereof. In some embodiments, the administration of an ACTH modulator comprises administration of a dopamine agonist, somatostatin, a somatostatin analog, retinoic acid, R-roscovitine, or a combination thereof. In some embodiments, the dopamine agonist is selected from the group consisting of bromocriptine and cabergoline. In some embodiments, the method comprises administering an additional medical or surgical therapy for treatment of hypercortisolemia in an absence of a detected reduction in the amount or activity of FKBP5 protein or reduction in the expression level of the gene encoding FKBP5 protein in the second sample.

In some embodiments the measuring of a) and/or c) comprises quantitating an amount of mRNA encoding FKBP5 protein in the sample. In some embodiments, the measuring of a) and/or c) comprises quantitating the amount of FKBP5 protein in the sample. In some embodiments the measuring comprises quantitating the amount of FKBP5 protein activity in the sample. In some embodiments, the quantitating the amount of FKBP5 protein activity in the sample comprises measuring FKBP5 protein peptidyl-prolyl-cis-trans isomerase activity in the sample. In some embodiments, the quantitating the amount of FKBP5 protein activity in the sample comprises measuring the amount of FKBP5 protein bound to glucocorticoid receptor (GR) in the sample.

In some embodiments, the GRA administration comprises administering mifepristone to the subject. In some embodiments, the GRA administration comprises administering a GRA that is not mifepristone to the subject. In some embodiments, GRA administration comprises administering a heteroaryl-ketone GRA. In some embodiments, the first or second samples comprise whole blood, or a fraction thereof. In some embodiments, the first and second samples comprise whole blood, or a fraction thereof. In some embodiments, the first or second samples comprise nasal epithelial scraping samples. In some embodiments, the patient is in need of a medical or surgical therapy for treatment of hypercortisolemia. In some embodiments, the patient has elevated levels of cortisol.

DEFINITIONS

Figure 1:
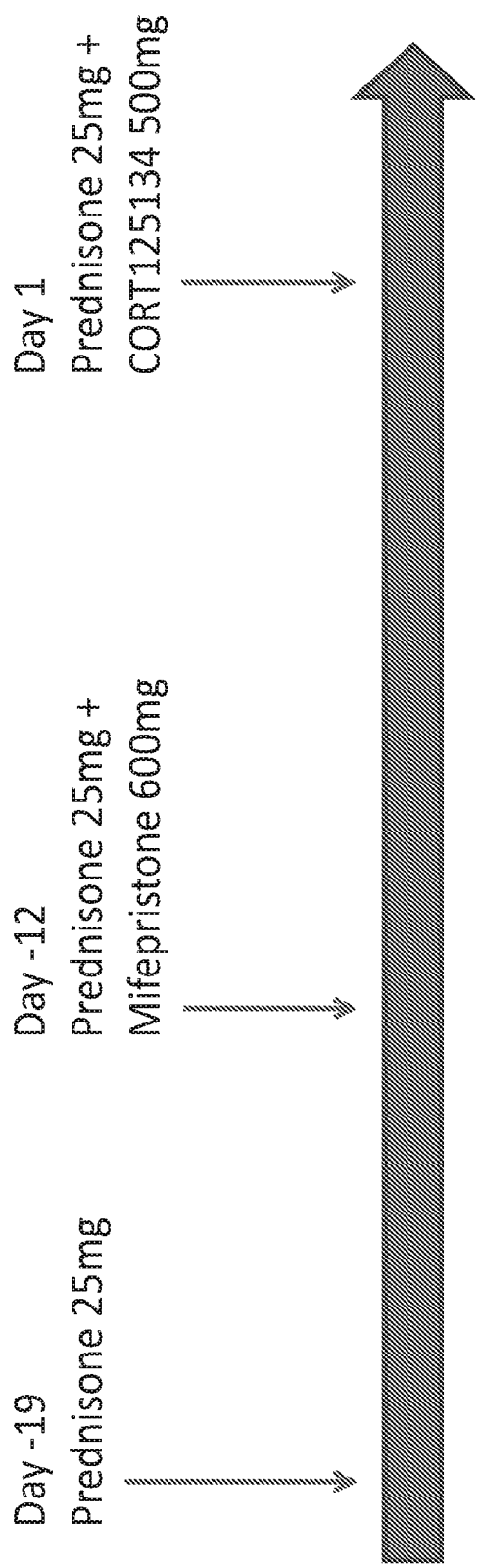
FIG. 1: depicts a study scheme for examining the expression level of the gene FKBP5, which encodes the FKBP5 protein, in response to administration of a GR modulator. In this scheme, healthy subjects are administered a GR agonist, followed by co-administration of a GR agonist and a GR antagonist (GRA). Blood samples are obtained from 10 subjects before each dose and at various time points after each dose. FKBP5 expression levels are measured before dosing on each day, and at selected times after dosing on each day.

The abbreviations used herein have their conventional meaning within the chemical and biological arts. As used in this specification and the appended claims, the singular forms "a," "an," and "the" include plural reference unless the context clearly dictates otherwise.

As used herein, "glucocorticoid receptor" ("GR") refers to the type II GR or nuclear receptor subfamily 3, group C, member 1 (NR3C1), which specifically binds to cortisol and/or cortisol analogs such as dexamethasone (See, e.g., Turner & Muller, J Mol Endocrinol Oct. 1, 2005 35 283-292). The GR is also referred to as the cortisol receptor. The term includes isoforms of GR, recombinant GR and mutated GR.

"Glucocorticoid receptor antagonist" ("GRA") refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10-fold greater ($\frac{1}{10}^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds GR with an affinity that is 100-fold greater ($\frac{1}{100}^{th}$ the $K_d$ value) than its affinity to the MR, AR, or PR, both the MR and PR, both the MR and AR, both the AR and PR, or to the MR, AR, and PR.

"Human subject" refers to a human primate. The human subject can be a person having, or suspected of having, Cushing's syndrome or a disease or condition that can be treated with a GRA. Similarly, "a patient in need of administration of a glucocorticoid receptor antagonist (GRA)" can be a person having or, or suspected of having, Cushing's syndrome or a disease or condition that can be treated with a GRA. Exemplary diseases or conditions that can be treated with a GRA include, but are not limited to cancer, breast cancer, triple negative breast cancer, prostate cancer, metastatic prostate cancer, ovarian cancer, Cushing's syndrome, or Cushing's disease. In some cases, the human subject can be a person that has been previously treated with transsphenoidal surgery (e.g., to remove tumors of the pituitary gland, such as pituitary adenomas). For example the subject may have undergone transsphenoidal surgery to treat Cushing's disease. In some cases, the human subject previously treated with transsphenoidal surgery can be a subject that has undergone transsphenoidal surgery less than, or less than about, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days, 2 days, or 1 day ago.

"Assessing a clinical or biochemical response to a glucocorticoid receptor antagonist (GRA)" refers to detecting or quantifying a response to an administered GRA. The clinical response can be an indication that the GRA is likely to be successful in treating a disease or condition, or successful in mitigating or ameliorating one or more symptoms of a disease or condition. The biochemical response can be an indication that the GRA is at a dose that is sufficient to alter, or significantly alter, the physiology of the subject to which the GRA is administered. The biochemical response can be an indication that the GRA is likely to be successful in treating a disease or condition, or successful in mitigating or ameliorating one or more symptoms of a disease or condition. The disease or condition can be, e.g., hypercortisolemia or Cushing's syndrome. The clinical or biochemical response can be assessed by detecting a change in GR activity or regulation caused by or correlated with administration of a GRA. For example, a change in the amount or activity of FKBP5 protein, or the expression level of a gene encoding FKBP5 protein, in response to administration of a GRA can be detected to assess a clinical response or a biochemical response to a GRA.

"Assessing a clinical or biochemical response to administering a medical or surgical therapy for treatment of hypercortisolemia" and the like, refers to detecting or quantitating a response to the administered therapy. The clinical response can be an indication that the therapy is likely to be successful in treating the hypercortisolemia, or successful in mitigating or ameliorating one or more symptoms of the hypercortisolemia. The biochemical response can be an indication that the administered therapy has altered, or significantly altered, the physiology of the subject to which the therapy is administered. The biochemical response can be an indication that the therapy is likely to be successful in treating the hypercortisolemia, or successful in mitigating or ameliorating one or more symptoms of the hypercortisolemia.

"Measuring an amount or activity of FKBP5 protein" refers to measuring the amount of FKBP5 protein or measuring the amount of an activity of the FKBP5 protein in a sample. The activity can be cis-trans prolyl isomerase activity, FK506 or rapamycin binding activity, GR binding activity, or chaperone activity (e.g., steroid hormone chaperone activity).

"Measuring an expression level of a gene encoding FKBP5 protein" generally refers to measurement of the amount of mRNA encoding FKBP5 protein in a sample, or measuring the production of mRNA encoding FKBP5 protein in the sample. Methods for measuring mRNA or mRNA production include, but are not limited to, RT-PCR, digital RT-PCR, RNA-seq (e.g., Methods Mol Biol. 2014; 1158: 71-91), and microarray analysis.

"Primary cells" refers to cells that have not been immortalized or passaged more than one time. Primary cells include human cells that have been taken directly from an individual without any subsequent culturing or division.

"Sample" refers to a biological sample obtained from any tissue or organ of a human subject. The sample can be any cell or tissue sample from a human subject. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification. The biological sample can contain primary cells originating from a human subject. The sample can contain an FKBP5 polypeptide or portion thereof, a nucleic acid encoding an FKBP5 polypeptide or portion thereof, an amplification or reverse transcription product of a nucleic acid encoding an FKBP5 polypeptide or portion thereof, or combination of any two or more of the foregoing polypeptides, nucleic acids, amplification products, reverse transcription products, or portions thereof.

"Whole blood" refers to blood collected from a human subject that is not subject to serum or plasma separation. "A fraction thereof" in the context of such whole blood refers to any fraction of whole blood, such as plasma, serum, a leukocyte fraction, a red blood cell fraction, a sample of peripheral blood mononuclear cells, and the like.

"Control" or "control value" in the context of amount or activity of FKBP5 protein, expression levels of the FKBP5 gene, or a fold-change in FKBP5 amount, activity, or expression level, can refer to a level that is typically found in a subject under various clinical conditions. For example, the control value can be an amount typically found in a Cushing's patient. As another example, the control value can be an amount typically found in a healthy (e.g., non-Cushing's) patient. As another example, the control value can be a fold-change typically observed when a patient or cells of a patient are administered a GRA (e.g., at a typical dose), wherein the patient or cells of the patient exhibit a clinical response to the GRA or exhibit a biochemical response to the GRA. As another example, a control value can be a fold-change that is typically observed when a patient or cells of a patient are administered a GRA (e.g., at a typical dose), wherein the patient or cells of the patient that do not exhibit a clinical response to the GRA or do not exhibit a biochemical response to the GRA.

In some cases, the control value is a normalized control value. The normalized control value can be normalized against a house keeping gene (e.g., GAPDH) or protein, or normalized against total protein or RNA (e.g., mRNA) levels as described herein. In some cases, the control value is an absolute value, or an absolute value per sample volume, or per number of cells in a sample.

DETAILED DESCRIPTION OF THE INVENTION

I. Introduction

The 51-kDa FK506 binding protein (FKBP51 or FKBP5) is part of the immunophilin family, a superfamily of highly conserved proteins first characterized by their ability to bind to immunosuppressant drugs (Batik, 2006; Baughman et al., 1995). In addition to their drug binding capabilities, some FK506 binding immunophilins are also protein chaperones, and have the related but apparently separate ability to isomerize proline residues (PPIase activity) (Barik, 2006).

The FKBP5 protein is an hsp90 co-chaperone that interacts with steroid hormone receptors, including the glucocorticoid receptor (GR), the progesterone receptor, and the androgen receptor (O'Leary, 2013). It is one of the chaperones that maintains un-liganded GR in the cytoplasm, thus reducing the affinity of GR for cortisol and reducing translocation of GR to the nucleus. Proline cis-trans isomerization is important for proper protein folding, but deletion of the N-terminal PPIase domain had little effect on the efficacy of the FKBP5 protein as a chaperone. It appears that the binding activity of the FKBP5 protein may be more important than its PPIase enzymatic activity in terms of GR signaling (O'Leary, 2013).

FKBP5 gene expression is induced by glucocorticoids (including cortisol) as part of an intracellular ultrashort negative feedback loop for GR activity (Vermeer, 2003). This induction is mediated by GR (Vermeer, 2003; Caldwell 2010). Chronic administration of corticosterone to mice, also results in elevated FKBP5 gene expression (Lee, 2010; Ewald, 2014).

Overexpression of FKBP5 in vitro reduces glucocorticoid binding affinity and nuclear translocation of GR. Naturally occurring over-expression of FKBP5 causes GR resistance in New World monkeys (Scammell, 2001), which is accompanied by increased cortisol levels. A role for FKBP5 in bone destruction, the development of osteoporosis in rheumatoid arthritis, and in glucocorticoid induced osteoporosis has been suggested (Kimura, 2013). Overexpression of FKBP5 in vivo in a rTg45 10 tau transgenic mouse model resulted in an increase in the level of phosphorylated tau and was associated with neuronal loss (Blair, 2013). In humans, overexpression of FKBP5 has been associated with Alzheimer's disease (Blair, 2013).

Polymorphisms of FKBP5 have been linked with several diseases, including depression (Binder 2004), post-traumatic stress disorder (Binder 2008), mood disorders (Binder 2009) and bipolar disorder (Willour, 2009). FKBP5 polymorphisms have also been linked to the response to anti-depressant treatment (Binder, 2004).

Yang et al demonstrated that fasting induces FKBP5 gene expression in the hypothalamus in mice and rats. Overexpression of the FKBP5 gene in mice on a high fat diet resulted in persistent elevated body weight and impaired glucose tolerance, suggesting that elevated FKBP5 expression and/or elevated FKBP5 protein levels or activity promotes an obese phenotype.

A recent study by Pereira et al (Metabolism, 2014) demonstrates that the FKBP5 gene is regulated by dexamethasone in human subcutaneous and omental adipose tissue. FKBP5 is among the top genes stimulated by the GR agonist dexamethasone. The authors also report that FKBP5 expression in adipose tissue is correlated with markers of insulin resistance. In addition, SNPs in the FKBP5 region were associated with type 2 diabetes and diabetes-related traits.

a. Treatment of Diseases with a Glucocorticoid Receptor Antagonist (GRA)

The GR is involved in a wide variety of diseases or conditions. In some cases, antagonizing GR activity or signaling (e.g., by administration of a glucocorticoid receptor antagonist (GRA)) can treat such diseases or conditions. However, there exists a great deal of variability in the susceptibility of certain diseases or conditions to treatment with a GRA. In some cases, the cells, tissue, or organ affected by the disease or condition can be, or can become, resistant to, or unaffected by, the administration of one or more GRAs. For example, although certain breast cancer cells (e.g., triple negative breast cancer cells) can be responsive to GRA treatment (e.g., in combination with one or more chemotherapeutics), not all such breast cancer cells are so responsive. Similarly, some diseases or conditions caused by or associated with elevated levels of cortisol exhibit variable treatment efficacy by administration of one or more GRAs. In some cases, identification of a clinical or biochemical response to the GRA can indicate that the GRA treatment should be continued. In some cases, a lack of a clinical or biochemical response can indicate that a different treatment (e.g., administration of a different GRA or administration of the same GRA at a higher dose) is indicated. Such responsiveness can vary from subject to subject, cell to cell, tissue to tissue, or during the course of a subject's disease progression. Thus there is a need for alternative methods for assessing a clinical or biochemical response to a GRA in a human subject.

Accordingly, described herein are methods of detecting or assessing a clinical or a biochemical response to administration of a glucocorticoid receptor antagonist (GRA) for treatment of a disease or condition. The methods for detecting or assessing a clinical or biochemical response to a GRA described herein involve detection of: (i) the activity or amount of FKBP5 protein; or (ii) the expression level of a gene encoding the FKBP5 protein (e.g., the absolute or relative amount of FKBP5 mRNA), in one or more provided samples from a human subject.

In some cases, the methods described herein involve detection of, or detection of a change in: (i) the activity or amount of FKBP5 protein; or (ii) the expression level of a gene encoding the FKBP5 protein (e.g., the absolute or relative amount of FKBP5 mRNA), in a subject. Such a change can be detected by determining the activity or amount of FKBP5 protein, or the expression level of a gene encoding FKBP5, in a first sample from a subject and comparing the results to the results from a second sample from the subject. The first sample can be provided or obtained from the subject prior to one or more steps of administering a GRA, and the second sample can be provided or obtained from the subject after one or more steps of administering a GRA.

b. Cushing's Syndrome

Also described herein are methods of diagnosing Cushing's syndrome. Cushing's syndrome is a condition caused by the excessive production of the glucocorticoid cortisol by the adrenal cortex. The condition is often due to the presence of a tumor or hyperplasia that exhibits unregulated secretion of adrenocorticotropic hormone (ACTH). The unregulated secretion of ACTH in turn induces the adrenal glands to secrete excess cortisol. Cortisol generally participates in a negative feedback loop, in which high levels of cortisol suppress secretion of both ACTH and cortisol. However, in Cushing's syndrome, this negative regulation is not effective or absent, resulting in chronic hypercortisolemia.

Cushing's syndrome can be diagnosed in a variety of ways. One method of diagnosis is known as the dexamethasone suppression test (DST). In this test, the glucocorticoid receptor agonist dexamethasone is administered to a patient and cortisol levels are measured after administration. The agonist can be administered in a low dose (e.g., 1-2 mg) to measure effects of a low dose on cortisol levels. In some cases, a high dose is also administered (e.g., 8 mg) to measure the effects of a high dose on cortisol levels. Moreover, ACTH levels can be determined prior to administration of dexamethasone for additional information. The presence of a low ACTH level and a cortisol level that is not suppressed by high or low dose dexamethasone indicates primary hypercortisolemia caused by, e.g., cortisol secreting adenoma tumors in the adrenal cortex. This type of Cushing's syndrome is not typically subject to ACTH or cortisol regulation.

The cortisol cut off for the DST has been a moving target. Currently the endocrine society recommends a cut off of 1.8 µg/dl and, the AACE guidelines recently decreased the cut off to 3 µg/dl (previously it was higher at 5 µg/dl). Endocrine societies in other countries use different cut offs. Thus, there is no general consensus of the most appropriate cut off to use. Moreover, the DST has high sensitivity but low specificity, therefore current guidelines for the diagnosis of Cushing's syndrome (CS) require at least 2 confirmatory tests (e.g., a DST and confirmation by an alternative diagnostic method).

In addition, the false positive rate of the 1 mg DST is high in certain populations (severe insulin resistance, fatty liver disease, PCOS etc., see "The Diagnosis of Cushing's Syndrome: An Endocrine Society Clinical Practice Guideline (2008), published as J. Clin. Endocrin. & Metab., May 2008, 93(5):1526-40.). Also medications that affect the metabolism of dexamethasone can influence the test (see guidelines from the Endocrine Society). Another important limitation for the 1 mg DST is the fact that 10-15% of confirmed Cushing's disease (CD) cases drop below the 2 µg/dl cut off with the 1 mg DST (Findling et al., J. Clin. Endocrinol. Met., 2004, 89:1222-1226) and thus would not be diagnosed by this test. Moreover, there is no consensus about the best diagnostic criterion for milder forms of Cushing's, especially adrenal Cushing's (see Endocrine Society guidelines, under adrenal incidentalomas).

An alternative to the dexamethasone suppression test (DST) is the 24 hours urine free cortisol (UFC) test. However, the UFC test has very low sensitivity in mild forms of CS. In addition the quality of the current assays is poor (see Raff et al. J. Clin. Endocrinol. Met., 2015, 100:395-397). It is a useful test for overt cases of CS, but there are often false negative results even in full blown cases, which can complicate the diagnostic process and delay the diagnosis. In addition, in cases of cyclical CS the diagnosis of CS can be missed if the test is done when the tumor is less active.

Another alternative to the DST is based on midnight salivary cortisol levels. This test also is less sensitive in milder forms of CS. It can be useful to diagnose early relapse of CD after transsphenoidal surgery. However, it has a lot of false positives and false negatives. It depends on whether the patient is able to perform the test properly, and inappropriate sample collection is frequently a confounding factor.

It is also possible to distinguish between Cushing's disease and Cushing's syndrome by administration of desmopressin or CRH. CRH can be useful in the differential diagnosis of Cushing's syndrome, because most patients with Cushing's disease respond to CRH, while those with other types of Cushing's syndrome generally do not. Although these tests, and in particular the dexamethasone suppression test, are widely used to diagnose Cushing syndrome and/or distinguish between Cushing's disease and other types of Cushing's syndrome, they are not definitive, and can yield an undesirable number of false positives and false negatives.

Accordingly, the present inventors have developed an improved method for diagnosing Cushing's syndrome. The method can include detecting: (i) the activity or amount of FKBP5 protein; or (ii) the expression level of a gene encoding the FKBP5 protein, in one or more samples from a human subject.

II. Methods a. Assessing a Clinical or a Biochemical Response to a GRA or to a Medical or Surgical Therapy for Treatment of Hypercortisolemia Described herein is a method for assessing a clinical or a biochemical response to a glucocorticoid receptor antagonist (GRA) in a human subject. The method can be useful, e.g., for confirming the efficacy of a treatment modality, monitoring treatment outcomes, or guiding treatment decisions. For example, if a patient presents with a disease or condition known to be, or suspected of being, treatable with a GRA, then a GRA can be administered, and the clinical response to the GRA can be assessed using one or more of the methods described herein. In some cases, a positive indication of a clinical or biochemical response, or an indication of a strong clinical or biochemical response, to the GRA can then predict a positive clinical outcome, an increased likelihood of a positive clinical outcome, or suggest continuation of GRA administration. In some cases, a negative indication of a clinical or biochemical response, or a lack of a strong clinical or biochemical response, can predict a negative clinical outcome, an increased likelihood of a negative clinical outcome, or suggest administration of an increased dose of the GRA or administration of an alternative GRA. In some cases, a negative indication of a clinical response or a biochemical response, or a lack of a strong clinical or biochemical response, can suggest a need for additional or alternative treatments.

The method for assessing a clinical or biochemical response to a glucocorticoid receptor antagonist (GRA) in a human subject can include: a) measuring a first amount, or activity of FKBP5 protein or a first expression level of a gene encoding FKBP5 protein in a first sample from the subject, wherein i) the first sample comprises primary cells; and ii) the first sample is obtained before administering the GRA to the subject; b) optionally administering the GRA to the subject; c) measuring a second amount or activity of FKBP5 protein or a second expression level of a gene encoding FKBP5 protein in a second sample from the subject, wherein: i) the second sample comprises primary cells; and ii) the second sample is obtained after administering the GRA to the subject; and d) comparing the first and second amounts, activities, or expression levels, wherein a reduction in the amount or activity of FKBP5 protein or a reduction in the expression level of the gene encoding FKBP5 protein in the second sample indicates the response to the GRA.

In some cases, the subject has received one or more doses of a GRA prior to the obtaining of a first sample. For example, the subject may be undergoing GRA therapy, or may have previously undergone GRA therapy. Thus, in some cases, the pre-GRA administration sample may be obtained a suitable period of time after a GRA administration to allow for measurement of baseline FKBP5 levels that are unaffected by the presence of a GRA. Thus, in some cases, the first sample, which is obtained prior to administering the GRA to the subject, is obtained at least 4, 5, 6, 7, 8, 9, 10, 12, 16, 18, or 24 hours after a previous GRA administration, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days after a previous GRA administration. A suitable period of time between a previous administration of a GRA and obtaining a first sample can be determined based on the pharmacokinetics of a previously administered GRA. In some cases, a suitable period of time is a length of time sufficient for the GRA to be completely removed from the subject. In some cases, a suitable period of time is a length of time sufficient for the GRA to have no or minimal effect on FKBP5 levels (e.g., amount or activity of FKBP5 protein or mRNA levels).

In some cases, the subject is administered multiple doses of a GRA between the obtaining of the first sample and the obtaining of the second sample. In some cases, the subject is administered, or is administered at least 1, 2, 3, 4, 5, 6, 7, 8, 9, 10, 11, 12, 13, 14, 15, 16, 17, 18, 19, 20, 21, 22, 23, 24, or more doses between the obtaining of the first sample and the obtaining of the second sample. In some cases, the subject is administered a GRA, and the second sample is obtained after a period of time suitable to allow for down-regulation of FKBP5. For example, the second sample can be obtained at least 0.5, 1, 2, 4, 6, 8, 10, 12, 16, 20, or 24 hours after GRA administration. In other cases, the second sample can be obtained between doses of a multiple GRA dosage schedule. In yet other cases, the second sample is obtained immediately prior, immediately after, or during one or more GRA administrations. In any case, the second sample is obtained after at least one dose of GRA has been administered to the subject.

Also described herein is a method for assessing a clinical or a biochemical response in a human subject to administering to the subject a medical or surgical therapy for treatment of hypercortisolemia. The method can be useful, e.g., for confirming the efficacy of a treatment modality, monitoring treatment outcomes, or guiding treatment decisions. For example, if a patient presents with hypercortisolemia, then a medical or surgical therapy can be administered, and the clinical response to the medical or surgical therapy can be assessed using one or more of the methods described herein. In some cases, a positive indication of a clinical or biochemical response, or an indication of a strong clinical or biochemical response, to the medical or surgical therapy can then predict a positive clinical outcome, an increased likelihood of a positive clinical outcome, or suggest continuation of the medical or surgical therapy. In some cases, a negative indication of a clinical or biochemical response, or a lack of a strong clinical or biochemical response, can predict a negative clinical outcome, an increased likelihood of a negative clinical outcome, or suggest administration of an increased dose or additional doses of a medical therapy, or administration of an alternative medical or surgical therapy. In some cases, a negative indication of a clinical response or a biochemical response, or a lack of a strong clinical or biochemical response, can suggest a need for additional or alternative treatments.

The method for assessing a clinical or biochemical response to a medical or surgical therapy for hypercortisolemia in a human subject can include: a) measuring a first amount, or activity of FKBP5 protein or a first expression level of a gene encoding FKBP5 protein in a first sample from the subject, wherein i) the first sample comprises primary cells; and ii) the first sample is obtained before administering the medical or surgical therapy to the subject; b) optionally administering the medical or surgical therapy to the subject; c) measuring a second amount or activity of FKBP5 protein or a second expression level of a gene encoding FKBP5 protein in a second sample from the subject, wherein: i) the second sample comprises primary cells; and ii) the second sample is obtained after administering the medical or surgical therapy to the subject; and d) comparing the first and second amounts, activities, or expression levels, wherein a reduction in the amount or activity of FKBP5 protein or a reduction in the expression level of the gene encoding FKBP5 protein in the second sample indicates the response to the medical or surgical therapy for treatment of hypercortisolemia.

In some cases, the medical or surgical therapy includes administering an inhibitor of steroidogenesis. Exemplary inhibitors of steroidogenesis include, but are not limited to, aminoglutethimide, cholesterol sulfate, ketoconazole, levoketoconazole, metyrapone, LCI699, mitotane, and etomidate. In some cases, the medical or surgical therapy includes administering an ACTH modulator. Exemplary ACTH modulators include, but are not limited to, dopamine agonists, retinoic acid, R-roscovitine, somatostatin, and somatostatin analogues. Exemplary dopamine agonists include, but are not limited to, bromocriptine, and cabergoline. Exemplary somatostatin analogues include, but are not limited to, pasireotide, octreotide, and lanreotide. In some cases, the medical or surgical therapy is or includes GRA administration. In some cases, the medical or surgical therapy is or includes transsphenoidal surgery, or repeat transsphenoidal surgery. In some cases, the medical or surgical therapy is or includes adrenalectomy, unilateral adrenalectomy, or bilateral adrenalectomy. In some cases, the medical or surgical therapy is or includes radiotherapy. In some cases, the medical or surgical therapy is or includes resection of a non-pituitary ACTH-secreting tumor. In some cases, the medical or surgical therapy is or includes treatment with a peptide receptor radionuclide therapy (e.g., Y-90 or Lu-177 labeled octreotide). In some cases, the medical or surgical therapy is or includes a combination of any two or more of the foregoing medical or surgical therapies. In some cases, the combination is a combination of two or more medical therapies. In some cases, the combination is a combination of two or more surgical therapies. In some cases, the combination is a combination of a medical therapy and a surgical therapy.

In some cases, the subject has received one or more doses of a medical therapy for hypercortisolemia prior to the obtaining of a first sample. For example, the subject may be undergoing GRA therapy, or may have previously undergone GRA therapy. Thus, in some cases, the pre-medical therapy administration sample may be obtained a suitable period of time after a medical therapy administration to allow for measurement of baseline FKBP5 levels that are unaffected by the presence of the medical therapy. Thus, in some cases, the first sample, which is obtained prior to administering the medical therapy to the subject, is obtained at least 4, 5, 6, 7, 8, 9, 10, 12, 16, 18, or 24 hours after a previous medical therapy administration, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days after a previous medical therapy administration. A suitable period of time between a previous administration of a medical therapy and obtaining a first sample can be determined based on the pharmacokinetics of a previously administered medical therapy. In some cases, a suitable period of time is a length of time sufficient for the medical therapy to be completely removed from the subject. In some cases, a suitable period of time is a length of time sufficient for the medical therapy to have no or minimal effect on FKBP5 levels (e.g., amount or activity of FKBP5 protein or mRNA levels).

In some cases, the subject is administered multiple doses of a medical therapy between the obtaining of the first sample and the obtaining of the second sample. In some cases, the subject is administered, or is administered at least 1, 2, 3, 4, 5, 6, 7, 8, 9, 10, 11, 12, 13, 14, 15, 16, 17, 18, 19, 20, 21, 22, 23, 24, or more doses between the obtaining of the first sample and the obtaining of the second sample. In some cases, the subject is administered a medical therapy, and the second sample is obtained after a period of time suitable to allow for downregulation of FKBP5 expression, amount, or activity. For example, the second sample can be obtained at least 0.5, 1, 2, 4, 6, 8, 10, 12, 16, 20, or 24 hours after administration of the medical therapy. In other cases, the second sample can be obtained between doses of a multiple dosage schedule. In yet other cases, the second sample is obtained immediately prior, immediately after, or during one or more administrations of a medical therapy. In any case, the second sample is obtained after at least one dose of a medical therapy has been administered to the subject.

i. Sample Extraction, Preparation, and Analysis

The sample can be obtained by any means known in the art. For example, the sample can be obtained by collecting a blood sample (e.g., a sample of whole blood or a fraction thereof). Alternatively, the sample can be obtained by scraping epithelial cells (e.g., nasal epithelial cells) of a subject. Samples include, but are not limited to samples of human cells and tissues, such as blood samples, cerebrospinal fluid samples, synovial tissue samples, synovial fluid samples, brain tissue samples, blood vessel samples, or tumor samples.

Samples encompass samples of healthy or pathological cells, tissues or structures. In some cases, the sample can be provided by obtaining cells of a tissue or organ affected by a disease or condition mediated by GR activity or signaling. For example, in human subjects suffering from a type of cancer that can be treated with a GRA (e.g., a GRA in combination with a chemotherapeutic), a sample containing primary tumor cells can be obtained and assayed as described herein. Such cancers include, but are not limited to, breast cancer, triple negative breast cancer, prostate cancer, metastatic prostate cancer, androgen resistant prostate cancer, and ovarian cancer. In some cases, the sample can be provided by obtaining cells of a subject suffering from hypercortisolemia. In some cases, the sample can be provided by obtaining cells of a tissue or organ affected by hypercortisolemia. In some cases, the sample can be provided by obtaining cells of a subject suffering from or suspected of being suffering from Cushing's syndrome. In some cases, the sample can be provided by obtaining cells of a tissue or organ affected by, or suspected of being affected by, Cushing's syndrome.

The sample can be extracted to obtain FKBP5 protein, or FKBP5 nucleic acid. For example, cells can be lysed, and the protein fraction obtained. In some cases, the lysate is further fractionated to purify a specified cellular compartment. For example, the cell lysate can be fractionated to obtain a cytosolic protein fraction. As another example, the cell lysate can be fractionated to obtain a nuclear or nucleolar protein fraction. The protein fraction can be assayed for FKBP5 protein levels or activity. Alternatively, the cells can be lysed, and a nucleic acid (e.g., mRNA) fraction obtained. The nucleic acid fraction can be assayed for expression of the gene encoding FKBP5. For example, the expression can be assayed by quantitative amplification (e.g., qPCR), or reverse transcription and subsequent quantitative amplification (e.g., RT-qPCR).

The cell lysate, or protein fraction thereof, can be purified using a variety of methods to obtain a fraction enriched for FKBP5 protein, or a portion thereof. For example, cells can be lysed and contacted with a chromatography medium under conditions suitable to preferentially bind contaminants or target protein. Where contaminants are preferentially bound, target protein can be collected as a flow through fraction and assayed further. Where target protein is bound, the chromatography medium can be washed and the target protein eluted.

As another example, cells can be lysed and contacted with a capture reagent (e.g., a capture antibody or aptamer) that specifically binds to the FKBP5 protein, or a portion thereof. The capture reagent can be immobilized on a solid support. In some cases, the FKBP5 protein or portion thereof can be eluted from the capture reagent and then detected or quantified. In other cases, the FKBP5 protein or portion thereof can be detected or quantified as a capture reagent-bound form.

Similarly, the cell lysate, or nucleic acid fraction thereof can be purified using a variety of methods to obtain a fraction enriched for a transcript of a gene encoding FKBP5. For example, cells can be lysed and nucleic acids can be precipitated or otherwise purified from the lysate. In some cases, the nucleic acids can be purified by contacting the sample, or a fraction thereof, with a surface immobilized oligodT moiety to preferentially bind polyadenylated mRNA.

Nucleic acids can be subject to amplification, hybridization, polymerization, reverse transcription, or a combination thereof. In some cases, the amplification, hybridization, polymerization, or reverse transcription is target specific such that the gene encoding FKBP5, a transcript thereof, or a portion thereof is specifically amplified, hybridized, or reverse transcribed. In some cases, the amplification, hybridization, polymerization, or reverse transcription is not target specific such that the sample is subject to whole genome or whole transcriptome hybridization, polymerization, or reverse transcription. Whole genome or other non-specific hybridization, polymerization, or reverse transcription can be performed with the use of one or more degenerate primers or probes. After non-specific hybridization, polymerization, or reverse transcription, the gene encoding FKBP5 can be detected and/or quantified.

The amount or activity of FKBP5 polypeptide, or a portion thereof, can be measured by a variety of methods known in the art. For example, an ELISA (e.g., sandwich ELISA) can be used to measure polypeptide levels in a sample, or a protein extract thereof, using one or more antibodies specific for the FKBP5 protein, or a portion thereof. In some cases, the ELISA is a sandwich ELISA, in which FKBP5 polypeptide, or a portion thereof, is immobilized by binding to an immobilized capture reagent (e.g., capture antibody or aptamer), and the immobilized polypeptide or portion thereof is detected with a detection reagent (e.g., detection antibody or aptamer).

As another example, activity of the FKBP5 polypeptide, or a portion thereof, can be measured by contacting the sample, or a protein extract thereof, with a proline containing peptide substrate to measure the FKBP5-mediated cis-trans prolyl isomerase activity of the sample. In some cases, the isomerization of the substrate can be measured using an cis-trans proline isomer sensitive enzyme, such as a protease. For example chymotrypsin, which has a high substrate specificity and catalytic efficiency ($k_{cat}$/Km) against peptide substrates having a trans-proline at the P2 position and phenylalanine or tyrosine at the P1 position, but very little or no specificity or catalytic efficiency against such peptides containing a cis-proline at P2, can be used to measure prolyl isomerase activity. For instance, an N-succinyl-Ala-Leu-cis-Pro-Phe-p-nitroanilide substrate can be used in combination with chymotrypsin, which preferably cleaves the trans prolyl isomer of the substrate to assay a sample or extract thereof for FKBP5 prolyl isomerase activity. The production of the trans isomer of the substrate by isomerase activity of the FKBP5 or portion thereof can be measured by detecting the digestion of the nitroanilide substrate by the chymotrypsin as described, e.g., in Fischer et al. Nature. 1989 Feb. 2; 337(6206):476-8.

As another example, activity of the FKBP5 polypeptide, or a portion thereof, can be detected or quantified by measuring the amount of FKBP5 protein bound to glucocorticoid receptor (GR) in the sample. This can be performed, e.g., by purifying GR or FKBP5 protein under conditions suitable to preserve binding between GR and FKBP5 protein. The purification product can then be assayed for the presence, absence, or quantity of the cognate binding partner. For example, cytosolic GR can be purified and the presence of FKBP5 protein detected in the purification product. As another example, FKBP5 protein can be purified and the presence of GR can be detected in the purification product. In some cases, this can be performed using a sandwich ELISA-type assay in which the immobilized capture reagent recognizes one member of the GR:FKBP5 protein complex and the detection reagent recognizes the other member of the GR:FKBP5 protein complex.

As another example, expression of a gene encoding FKBP5 can be measured by reverse transcription of FKBP5 mRNA, or a portion thereof, and quantitative amplification of the reverse transcription product or a portion thereof. The quantitative amplification can be performed using PCR (e.g., real time PCR) or other amplification techniques known in the art. The amplification can be detected by, e.g., detecting incorporation of an intercalating dye into the amplification product, degradation of a quenched fluorescence hydrolysis probe, or binding of quenched molecular beacon.

Any measured amount or activity or expression level in a sample can be normalized to a reference. For example, an expression level can be normalized to the amount of total mRNA, or the expression level of a reference gene. Suitable reference genes include, but are not limited to, GAPDH, hypoxanthine phosphoribosyltransferase 1 (HRPT1), ribosomal protein large P1, or another housekeeping gene. As another example, FKBP5 protein amount can be normalized to total protein levels, or the level of a reference gene product. Suitable reference gene products include, but are not limited to, actin, tubulin, COX IV, HRPT1, GAPDH, or another housekeeping gene product.

ii. Comparing FKBP5 Amount Activity or Expression

In some embodiments, the amount or activity of FKBP5 or the expression level of a gene encoding FKBP5 protein after administration of a GRA is quantified from a sample obtained after administration of one or more doses of the GRA and compared to a control or threshold value rather than a pre-GRA administration value. In some cases, the control or threshold value is a positive control or threshold value that indicates a biochemical or clinical response, or a strong biochemical or clinical response to the GRA in the tissue, organ, or cell-type subject to the assay. Thus in such cases, a quantified amount, activity, or expression level that is near, equal to, or below the positive control or threshold value can indicate a biochemical or clinical response or a strong biochemical or clinical response to the GRA. In contrast, a quantified amount, activity, or expression level that is above, or significantly above, the positive control or threshold value can indicate a lack of a biochemical or clinical response, or a lack of a strong biochemical or clinical response to the GRA.

In some cases, the quantified amount, activity, expression that indicates a biochemical or clinical response to the GRA is equal to about, or less than about, 25%, 30%, 40%, 50%, 75%, 100%, 110%, 125%, or 150% of the positive control or threshold value. In some cases, the quantified amount, activity, or expression that indicates a lack of a biochemical or clinical response to the GRA is equal to about or above about a 2-fold, 2.5-fold, 3-fold, 4-fold, 5-fold, 7.5-fold, 10-fold, 12-fold, 15-fold, 20-fold, 25-fold, 30-fold, 40-fold, or 50-fold multiple of the positive control or threshold value.

In some cases, the control or threshold value is a negative control or threshold value that indicates a lack of a response (e.g., biochemical or clinical) to a GRA or a value that is typically obtained without, or prior to, administration of a GRA. Thus in such cases, a quantified amount, activity, or expression level that is below the negative control or threshold value (e.g., significantly below) can indicate a clinical or biochemical response or a strong clinical or biochemical response to the GRA. In contrast, a quantified amount, activity, or expression level that is near, equal to, or above the negative control or threshold value can indicate a lack of a clinical response, a lack of biochemical response, a lack of a strong clinical response, or a lack of a strong biochemical response to the GRA. In some cases, the quantified amount, activity, or expression that indicates a clinical response to the GRA or a biochemical response to the GRA is equal to about or less than about 0.25%, 0.5%, 1%, 5%, 7.5%, 10%, 12.5%, 15%, 17.5%, 20%, 25%, 30%, 40%, or 50% of the negative control or threshold value. In some cases, the quantified amount, activity, or expression that indicates a lack of a clinical response or a lack of a biochemical response to the GRA is at least about 75%, 100%, 110%, 125%, 150%, 200%, 300%, or 400% of the negative control or threshold value.

In some embodiments, the amount or activity of FKBP5 protein or the expression level of a gene encoding FKBP5 after administration of a GRA is quantified from a sample obtained after administration of one or more doses of the GRA and compared to a value quantified from a sample obtained prior to administration of one or more doses of the GRA. A quantified post-administration amount activity or expression level that is below the pre-administration value can indicate a clinical response, a biochemical response, a strong clinical response, or a strong biochemical response to the GRA. In contrast, a quantified post-administration amount activity or expression level that is near or equal to the pre-administration value can indicate a lack of a clinical response, a lack of a biochemical response, a lack of a strong biochemical response, or a lack of a strong clinical response to the GRA. In some cases, when the post-GRA administration value is greater than the pre-GRA administration value, progression of the disease or condition in the human subject is indicated. In some cases, when the post-GRA administration value is less than the pre-GRA administration value, improvement of the disease or condition in the human subject is indicated.

The provided pre-GRA administration sample can be taken at any time prior to administration of a GRA, including but not limited to, immediately before GRA administration; at least about 1, 2, 3, 4, 6, 7, 8, 10, 15, 20, 25, 30, 45, 50, 60, 80, or 90 minutes before GRA administration; at least about 2, 3, 4, 5, 6, 7, 8, 10, 12, 14, 16, 18, 20, or 22 hours before GRA administration; at least about 1, 2, 3, 4, 5, or 6 days before GRA administration; or at least about 1, 1.5, 2, 3, or 4 weeks before GRA administration. In some cases, the provided pre-administration sample is obtained from about 0 to about 12, from about 0 to 6 hours, from about 0 to about 4 hours, from about 1 to 4 hours, or from about 2 to 6 hours prior to administration of the GRA.

The provided post-GRA administration sample can be taken after a time suitable to allow the activity of the GRA to manifest in a change (e.g., a detectable change) in FKBP5 amount or activity, or a change in expression of a gene encoding FKBP5. In some cases, the time is selected to achieve a maximum possible response (e.g., clinical or biochemical response) to GRA administration. In some cases, the delay between administration of the GRA and obtaining of the post-GRA administration sample is at least about 1, 2, 3, 4, 5, 6, 7, 8, 9, 10, 11, 12, 13, 15, 20, 25, 30, 40, or 50 minutes; 1, 2, 3, 4, 5, 6, 7, 8, 10, 12, 14, 15, 16, 18, 20, or 22 hours; 1, 2, 3, 4, 5, or 6 days; or 1, 2, 3, or 4 weeks.

The provided post-GRA administration sample can be taken after multiple administrations of one or more GRAs. For example, one or more GRAs can be administered to a human subject in need thereof for a period of days (e.g., 1, 2, 3, 4, 5, or 6 days) or weeks (e.g., 1, 2, 3, 4, or 5 weeks) and then a post-administration sample obtained and analyzed for FKBP5 protein amount or activity or FKBP5 gene expression to assess a clinical response to the GRA or to assess a biochemical response to the GRA.

In some cases, the quantified post-GRA administration amount, activity, or expression that indicates a clinical or biochemical response to the GRA is less than about, 300%, 250%, 200%, 150%, 100%, 75%, 50%, 40%, 30%, 25%, 20%, 15%, 10%, 7.5%, 5%, 2.5%, 2%, 1.5%, or 1% of the pre-GRA administration value. In some cases, the quantified post-GRA administration amount activity or expression that indicates a lack of a clinical or biochemical response to the GRA is equal to about or above about 75%, 80%, 85%, 90%, 100%, 110%, 120%, 125%, 150%, or 200% of the pre-GRA administration value.

In some cases, the human subject can have cancer, and methods described herein can be employed to assess or predict the effect of GRA therapy on the cancer cells of the subject. In some cases, cancer cells are obtained from a subject and assayed for FKBP5 amount or activity or the expression level of a gene encoding FKBP5. In some cases, a high level of FKBP5 relative to a control may suggest that the cells express a high level of GR and GRA therapy may be indicated. In some cases, a low level of FKBP5 relative to a control may suggest that the cells express a low level of GR and GRA therapy is not indicated. In some cases, a low level of FKBP5 relative to a control may suggest that the FKBP5 feedback mechanism is inoperative, and thus GRA therapy may be indicated. In some cases, a reduction in FKBP5 in tumor cells after administration of GRA as compared to a pre-administration value can suggest that GRA therapy is indicated.

Similarly, FKBP5 amount, activity, or expression level can be assessed in combination with GR amount, activity, or expression level. In some cases, low GR amount, activity, or expression level and low FKBP5 amount, activity, or expression level can predict that GRA therapy is not beneficial for this cancer type, cell, or tumor. In some cases, high GR amount, activity, or expression level and high FKBP5 amount, activity, or expression level can indicate that GRA therapy can be beneficial for this cancer type, cell, or tumor. In some cases, high GR amount, activity, or expression level and low FKBP5 amount, activity, or expression level can indicate a defective cortisol counter regulation mechanism and GRA therapy can be a beneficial treatment.

In some cases, FKBP5 levels can be detected in tumor cells that have been extracted from a patient and cultured in vitro. For example, a sample containing tumor cells can be obtained, a portion of the sample assayed for FKBP5 (protein or expression), and a GRA administered to a different portion of the sample. The GRA administered sample can be assayed for FKBP5 protein amount, or activity, or FKBP5 gene expression and compared to the pre-administration value.

In some cases, FKBP5 levels can be determined after transsphenoidal surgery to detect relapse or remission of Cushing's syndrome. For example, FKBP5 can be measured in samples obtained before and after transsphenoidal surgery. Additionally or alternatively, FKBP5 can be detected in samples obtained at several time points after transsphenoidal surgery. For example, FKBP5 can be detected in one or more samples obtained within 1, 2, 3, 4, 5, 6, 7, 8, 9, 10, 11, 12, 13, 14, 15, 16, 17, 18, 19, or 20 days after transsphenoidal surgery. In some cases, a low level of FKBP5 relative to a control can indicate that the subject is exhibiting remission of Cushing's syndrome or is not exhibiting early relapse of Cushing's syndrome. In some cases, a decrease in FKBP5 as compared to the value detected in a sample obtained prior to transsphenoidal surgery indicates that the subject is exhibiting remission of Cushing's syndrome or is not exhibiting early relapse of Cushing's syndrome. In some cases, a stable or decreasing value of FKBP5 in samples taken at multiple time points after transsphenoidal surgery indicates that the subject is exhibiting remission of Cushing's syndrome or is not exhibiting early relapse of Cushing's syndrome.

In some embodiments, in the absence of a detected reduction in the amount or activity of FKBP5 protein or expression of the gene encoding FKBP5 protein after administration of the GRA and relative to a pre-GRA administration or control value, the method comprises administering an increased amount of GRA to the subject, or administering an alternative GRA to the subject, or a combination thereof. In some embodiments, in the absence of a detected reduction that is greater than a threshold value in the amount or activity of FKBP5 protein or expression of the gene encoding FKBP5 protein after administration of the GRA and relative to a pre-GRA administration or control value, the method comprises administering an increased amount of GRA to the subject, or administering an alternative GRA to the subject, or a combination thereof.

In some embodiments, the amount or activity of FKBP5 or the expression level of a gene encoding FKBP5 protein after administration of a medical (e.g., GRA) or surgical therapy for treatment of hypercortisolemia is quantified from a provided sample obtained after administration of one or more doses of a medical therapy for treatment of hypercortisolemia and compared to a control or threshold value rather than a pre-administration value. In some cases, the control or threshold value is a positive control or threshold value that indicates a biochemical or clinical response, or a strong biochemical or clinical response to the medical or surgical therapy in the tissue, organ, or cell-type subject to the assay. Thus in such cases, a quantified amount, activity, or expression level that is near, equal to, or below the positive control or threshold value can indicate a biochemical or clinical response or a strong biochemical or clinical response to the medical or surgical therapy for treatment of hypercortisolemia. In contrast, a quantified amount, activity, or expression level that is above, or significantly above, the positive control or threshold value can indicate a lack of a biochemical or clinical response, or a lack of a strong biochemical or clinical response to the medical or surgical therapy for treatment of hypercortisolemia.

In some cases, the quantified amount, activity, expression that indicates a biochemical or clinical response to the medical or surgical therapy for treatment of hypercortisolemia is equal to, about, or less than about, 25%, 30%, 40%, 50%, 75%, 100%, 110%, 125%, or 150% of the positive control or threshold value. In some cases, the quantified amount, activity, or expression that indicates a lack of a biochemical or clinical response to the medical or surgical therapy for treatment of hypercortisolemia is equal to, about, or above about a 2-fold, 2.5-fold, 3-fold, 4-fold, 5-fold, 7.5-fold, 10-fold, 12-fold, 15-fold, 20-fold, 25-fold, 30-fold, 40-fold, or 50-fold multiple of the positive control or threshold value.

In some cases, the control or threshold value is a negative control or threshold value that indicates a lack of a response (e.g., biochemical or clinical) to a medical or surgical therapy for treatment of hypercortisolemia or a value that is typically obtained without, or prior to, administration of a medical or surgical therapy for treatment of hypercortisolemia. Thus in such cases, a quantified amount, activity, or expression level that is below the negative control or threshold value (e.g., significantly below) can indicate a clinical or biochemical response or a strong clinical or biochemical response to the medical or surgical therapy for treatment of hypercortisolemia. In contrast, a quantified amount, activity, or expression level that is near, equal to, or above the negative control or threshold value can indicate a lack of a clinical response, a lack of biochemical response, a lack of a strong clinical response, or a lack of a strong biochemical response to the medical or surgical therapy for treatment of hypercortisolemia. In some cases, the quantified amount, activity, or expression that indicates a clinical response to the medical or surgical therapy for treatment of hypercortisolemia or a biochemical response to the medical or surgical therapy for treatment of hypercortisolemia is equal to, about, or less than about 0.25%, 0.5%, 1%, 5%, 7.5%, 10%, 12.5%, 15%, 17.5%, 20%, 25%, 30%, 40%, or 50% of the negative control or threshold value. In some cases, the quantified amount, activity, or expression that indicates a lack of a clinical response or a lack of a biochemical response to the medical or surgical therapy for treatment of hypercortisolemia is at least about 75%, 100%, 110%, 125%, 150%, 200%, 300%, or 400% of the negative control or threshold value.

In some embodiments, the amount or activity of FKBP5 protein or the expression level of a gene encoding FKBP5 after administration of a medical therapy for treatment of hypercortisolemia is quantified from a sample obtained after administration of one or more doses of the medical therapy for treatment of hypercortisolemia and compared to a value quantified from a sample obtained prior to administration of one or more doses of the medical therapy for treatment of hypercortisolemia. A quantified post-administration amount activity or expression level that is below the pre-administration value can indicate a clinical response, a biochemical response, a strong clinical response, or a strong biochemical response to the medical therapy for treatment of hypercortisolemia. In contrast, a quantified post-administration amount activity or expression level that is near or equal to the pre-administration value can indicate a lack of a clinical response, a lack of a biochemical response, a lack of a strong biochemical response, or a lack of a strong clinical response to the medical therapy for treatment of hypercortisolemia. In some cases, when the post-administration value is greater than the pre-administration value, progression of the hypercortisolemia condition in the human subject is indicated. In some cases, when the post-administration value is less than the pre-administration value, improvement of the hypercortisolemia condition in the human subject is indicated.

The pre-administration sample can be taken at any time prior to administration of a medical or surgical therapy for treatment of hypercortisolemia, including but not limited to, immediately before therapy administration; at least about 1, 2, 3, 4, 6, 7, 8, 10, 15, 20, 25, 30, 45, 50, 60, 80, or 90 minutes before therapy administration; at least about 2, 3, 4, 5, 6, 7, 8, 10, 12, 14, 16, 18, 20, or 22 hours before therapy administration; at least about 1, 2, 3, 4, 5, or 6 days before therapy administration; or at least about 1, 1.5, 2, 3, or 4 weeks before therapy administration. In some cases, the pre-administration sample is obtained from about 0 to about 12, from about 0 to 6 hours, from about 0 to about 4 hours, from about 1 to 4 hours, or from about 2 to 6 hours prior to administration of the therapy.

The post-therapy administration sample can be taken after a time suitable to allow the activity of the therapy to manifest in a change (e.g., a detectable change) in FKBP5 amount or activity, or a change in expression of a gene encoding FKBP5. In some cases, the time is selected to achieve a maximum possible response (e.g., clinical or biochemical response) to therapy administration. In some cases, the delay between administration of the therapy and obtaining of the post-therapy administration sample is at least about 1, 2, 3, 4, 5, 6, 7, 8, 9, 10, 11, 12, 13, 15, 20, 25, 30, 40, or 50 minutes; or 1, 2, 3, 4, 5, 6, 7, 8, 10, 12, 14, 15, 16, 18, 20, 22, or 24 hours.

The post-therapy administration sample can be taken after multiple administrations of one or more medical or surgical therapies. For example, one or more medical therapies (e.g., administration of a GRA, ACTH-modulator, inhibitor of steroidogenesis, etc.) can be administered to a human subject in need thereof for a period of days (e.g., 1, 2, 3, 4, 5, or 6 days) or weeks (e.g., 1, 2, 3, 4, or 5 weeks) and then a post-administration sample obtained and analyzed for FKBP5 protein amount or activity or FKBP5 gene expression to assess a clinical response to the medical therapy or to assess a biochemical response to the medical therapy. As another example, one or more surgical therapies (e.g., transsphenoidal surgery, resection of a non-pituitary ACTH-secreting tumor, etc.) can be administered to a human subject in need thereof and then repeated, and then a post-administration sample obtained and analyzed for FKBP5 protein amount or activity or FKBP5 gene expression to assess a clinical response to the surgical therapy or to assess a biochemical response to the surgical therapy.

In some cases, the quantified post-administration amount, activity, or expression that indicates a clinical or biochemical response to the therapy is less than about, 75%, 50%, 40%, 30%, 25%, 20%, 15%, 10%, 7.5%, 5%, 2.5%, 2%, 1.5%, or 1% of the pre-administration value. In some cases, the quantified post-administration amount activity or expression that indicates a lack of a clinical or biochemical response to the therapy is equal to, about, or above about 80%, 85%, 90%, 100%, 110%, 120%, 125%, 150%, or 200% of the pre-administration value.

In some cases, FKBP5 levels can be determined after transsphenoidal surgery to detect relapse or remission of hypercortisolemia. For example, FKBP5 can be measured in samples obtained before and after transsphenoidal surgery. Additionally or alternatively, FKBP5 can be detected in samples obtained at several time points after transsphenoidal surgery. For example, FKBP5 can be detected in one or more samples obtained within 1, 2, 3, 4, 5, 6, 7, 8, 9, 10, 11, 12, 13, 14, 15, 16, 17, 18, 19, or 20 days after transsphenoidal surgery. In some cases, a low level of FKBP5 relative to a control can indicate that the subject is exhibiting remission of hypercortisolemia or is not exhibiting early relapse of hypercortisolemia. In some cases, a decrease in FKBP5 as compared to the value detected in a sample obtained prior to transsphenoidal surgery indicates that the subject is exhibiting remission of hypercortisolemia or is not exhibiting early relapse of hypercortisolemia. In some cases, a stable or decreasing value of FKBP5 in samples taken at multiple time points after transsphenoidal surgery indicates that the subject is exhibiting remission of hypercortisolemia or is not exhibiting early relapse of hypercortisolemia.

In some embodiments, in the absence of a detected reduction in the amount or activity of FKBP5 protein or expression of the gene encoding FKBP5 protein after administration of the medical or surgical therapy for treatment of hypercortisolemia and relative to a pre-administration or control value, the method comprises administering an increased amount of a medical therapy to the subject, administering an alternative medical therapy to the subject, administering an additional surgical therapy to the subject, or administering an alternative surgical therapy to the subject, or a combination thereof. In some embodiments, in the absence of a detected reduction in the amount or activity of FKBP5 protein or expression of the gene encoding FKBP5 protein after administration of the medical or surgical therapy for treatment of hypercortisolemia and relative to a pre-administration or control value, wherein the detected reduction is greater than a threshold value, the method comprises administering an increased amount of a medical therapy to the subject, administering an alternative medical therapy to the subject, administering an additional surgical therapy to the subject, or administering an alternative surgical therapy to the subject, or a combination thereof.

iii. Threshold, Control, and Threshold Difference Values

FKBP5 amount, expression, or activity can be compared to various threshold, control, or threshold difference values to assess clinical or biochemical response as described herein. Similarly, a change in FKBP5 amount, expression, or activity from pre-administration (e.g., pre-GRA administration or pre-medical or surgical therapy for treatment of hypercortisolemia administration) to post-administration can be compared to various threshold, control, or threshold difference values to assess a clinical or biochemical response to the administered GRA or other therapy as described herein. In some cases, the threshold, control, or threshold difference value is selected to provide a sufficient sensitivity or specificity for use as a diagnostic. For example, the threshold, control, or threshold difference value can be selected to provide at least a 90% sensitivity, at least a 95% specificity, or the combination thereof. In some cases, the threshold, control, or threshold difference value is derived from a cohort of test individuals, wherein the cohort is of sufficient size to provide the sufficient sensitivity or specificity for use as a diagnostic.

In some cases, the cohort size is at least 100 or at least 200 test individuals. For example, 100 or 200 healthy (e.g., non-Cushing's, non-hypercortisolemic, or not otherwise in need of a GRA) test individuals can be selected to provide a threshold or control amount, activity, or expression level of FKBP5. As described herein, a measured FKBP5 amount, activity, or expression level in a human subject that is high as compared to a threshold or control level derived from a cohort of at least 100 or at least 200 healthy test individuals can indicate the subject has Cushing's syndrome. Alternatively, as described herein, a cohort of such healthy individuals would be expected to exhibit a small difference in FKBP5 amount, expression, or activity in response to administration of a medical or surgical therapy such as a GRA. As such, a measured reduction in FKBP5 amount, activity, or expression level from pre-administration to post-administration that is greater than (e.g., at least 2-fold, 3-fold, 5-fold, 10-fold, 25-fold, or 50-fold greater than) a threshold difference (e.g., threshold reduction) value derived from a cohort of at least 100 or at least 200 healthy test individuals in response to therapy administration can indicate a clinical or biochemical response to the GRA.

In some cases, the cohort size is at least 20 or 30 or 50 test individuals. For example, the cohort can comprise or consist of subjects known or suspected of having Cushing's syndrome. In some cases, the cohort of test individuals known or suspected of having Cushing's syndrome is an untreated control cohort. In some cases, the cohort can comprise or consist of subjects having Cushing's syndrome and exhibiting a clinical or biochemical response to an administered GRA or other medical or surgical therapy for treatment of Cushing's, e.g., as indicated by a reduction in, or elimination of, one or more symptoms of Cushing's. As described herein, a measured FKBP5 amount, activity, or expression level that is similar to (e.g., less than 5%, 10%, 25%, 30%, 50%, 75%, or 100% above, or at least 95%, 90%, 80%, 70%, 60%, or 50% of) a threshold value derived from a cohort of 20 or 30 or 50 test individuals known or suspected of having (e.g., untreated) Cushing's syndrome can indicate that the subject has Cushing's syndrome. In contrast, a measured FKBP5 amount, activity, or expression level that is lower than (e.g., less than 1%, 5%, 10%, 15%, 20%, 25%, or 50% of) a threshold value derived from a cohort of 20 or 30 or 50 test individuals known or suspected of having (e.g., untreated) Cushing's syndrome can indicate that the subject does not have Cushing's syndrome.

Alternatively, a measured reduction in FKBP5 amount, activity, or expression level from pre-GRA administration to post-GRA administration that is similar to a threshold difference value derived from a cohort of 20 to 30, 20 to 50, 30 to 50, or at least 20, 30, or 50 individuals known or suspected of having Cushing's syndrome and exhibiting a clinical or biochemical response to GRA administration can indicate a clinical or biochemical response to the GRA. In contrast, if the reduction from pre-GRA administration to post-GRA administration does not meet the threshold difference value derived from the cohort of 20 to 30, 20 to 50, 30 to 50, or at least 20, 30, or 50 individuals known or suspected of having Cushing's syndrome and exhibiting a clinical or biochemical response to GRA administration, a lack of a clinical or biochemical response to the GRA is indicated.

The threshold, control, or threshold difference value derived from the cohort (e.g., a cohort of at least 100 or at least 200 healthy individuals or a cohort of at least 20 to 30, 20 to 50, 30 to 50, or at least 20, 30, or 50 individuals known or suspected of having Cushing's syndrome) can be a contained in a database. In such cases, comparisons to the threshold, control, or threshold difference value can comprise querying the database. In some cases, the comparison further comprises applying a test of statistical significance. In some cases, the test of statistical significance includes a comparison of the relative variability of the amount, activity, or expression level in the cohort to the amount, activity, or expression level in the human subject. In some cases, the test of statistical significance includes a comparison of the relative variability in a change in FKBP5 amount, activity, or expression from pre- to post-medical or surgical therapy administration or from pre- or post-GRA administration in the cohort to the change in the amount, activity, or expression level of FKBP5 in the human subject. In some cases, the methods include identifying whether the comparison is statistically significant in view of the inherent variability of the measurement as indicated by the observed variability in the cohort.

iv. GRA Administration

A GRA administered to the human subject can be any glucocorticoid receptor antagonist, including any of the GRAs described herein. Exemplary GRAs include, but are not limited to, mifepristone, or a heteroaryl-ketone GRA. In some cases, the GRA administered to the human subject is not mifepristone. In some cases, the GRA is a specific GRA that preferentially binds to, and antagonizes, the GR rather than other nuclear receptors, such as mineralocorticoid receptor (MR), androgen receptor (AR), or progesterone receptor (PR). In some cases, the GRA is a pan-specific GRA that preferentially binds to, and antagonizes, the GR and one or two other nuclear receptors selected from the group consisting of MR, AR, and PR. In some cases, the GRA is a non-specific GRA that binds to and antagonizes GR, MR, AR, and PR.

The GRA can be a steroidal GRA, such as a compound containing a modified cortisol steroid backbone. The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563). Steroidal GRAs can also include androgen-type steroid compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GRAs include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and 17β-hydroxy-17α-19-(4-methylphenyl) androsta-4,9(11)-dien-3-one (RU044).

Other examples of steroidal GRAs are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., Int'l J. of Neuro-psychopharmacology, 5:Supp. 1, 5148 (2002); disclose the compound (11β,17β)-11-(1,3-benzodioxol-5-yl)-17-hydroxy-17-(1-propynyl)estra-4,9-dien-3-one (ORG 34517).

The GRA can be a non-steroidal GRA. Non-steroidal GRAs do not share structural homology to, or are not modifications of, cortisol. Such compounds include synthetic mimetics and analogs of proteins, including partially peptidic, pseudopeptidic and non-peptidic molecular entities. Non-steroidal GRA compounds also include glucocorticoid receptor antagonists having a cyclohexyl-pyrimidine backbone, a fused azadecalin backbone, a heteroaryl ketone fused azadecalin backbone, or an octahydro fused azadecalin backbone. Exemplary glucocorticoid receptor antagonists having a cyclohexyl-pyrimidine backbone include those described in U.S. Pat. No. 8,685,973. Exemplary glucocorticoid receptor antagonists having a fused azadecalin backbone include those described in U.S. Pat. Nos. 7,928,237; and 8,461,172. Exemplary glucocorticoid receptor antagonists having a heteroaryl ketone fused azadecalin backbone include those described in U.S. 2014/0038926. Exemplary glucocorticoid receptor antagonists having an octohydro fused azadecalin backbone include those described in U.S. Provisional Patent Appl. No. 61/908,333, entitled Octahydro Fused Azadecalin Glucocorticoid Receptor Modulators, Attorney Docket No. 85178-887884 (007800US), filed on Nov. 25, 2013.

Examples of non-steroidal GRAs include the GR antagonist compounds disclosed in U.S. Pat. Nos. 5,696,127; 6,051,573; and 6,570,020; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2 (R)-chloroethynyl-1,2,3,4,4α,9,10,10α(R)-octahydro-phenanthrene-2,7-diol ("CP 394531") and 4a(S)-benzyl-2 (R)-prop-1-ynyl-1,2,3,4,4α,9,10,10α(R)-octahydro-phenanthrene-2,7-diol ("CP 409069"); and the compounds disclosed in PCT International Application No. WO 96/19458, which describes non-steroidal compounds which are high-affinity, highly selective antagonists for steroid receptors, such as 6-substituted-1,2-dihydro-N-protected-quinolines.

The GRAs can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of a GRA. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The GRA can be co-administered with other agents. Co-administration includes administering the GRA within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the GRA can each be administered once a day, or two, three, or more times per day so as to provide the preferred dosage level per day.

In some embodiments, co-administration can be accomplished by co-formulation, i.e., preparing a single pharmaceutical composition including a GRA and any other agent. Alternatively, the various components can be formulated separately. Exemplary compounds, compositions, or active agents that can be co-administered with a GRA include, but are not limited to, another GRA, an agent that inhibits cellular proliferation, an anti-cancer chemotherapeutic, or an antibody.

The GRA, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg. If the GRA is mifepristone, treatment can be further understood by reference to U.S. application Ser. No. 13/677,465, the disclosure of which is incorporated by reference in its entirety.

The composition can also contain other compatible therapeutic agents. The therapeutic agents can be used in combination with one another, with other active agents known to be useful in antagonizing a glucocorticoid receptor, or with adjunctive agents that may not be effective alone, but may contribute to the efficacy of the active agent.

b. Diagnosis of Cushing's Syndrome

Cushing's syndrome can be diagnosed by detecting an amount or activity of FKBP5 protein or an expression level of a gene encoding FKBP5 and correlating the amount, activity, or expression level with a presence or absence, or likelihood, of Cushing's syndrome. The method can include: a) measuring an amount, or activity of FKBP5 protein or an expression level of a gene encoding FKBP5 in a sample from the subject; and b) identifying the subject as likely to be suffering from Cushing's syndrome when the amount, activity, or expression level is indicative of Cushing's syndrome.

The sample can be obtained by a variety of means. For example, the sample can be obtained by collecting a blood sample (e.g., a sample of whole blood or a fraction thereof). Alternatively, the sample can be obtained by scraping epithelial cells (e.g., nasal epithelial cells) of a subject. Samples include, but are not limited to samples of human cells and tissues, such as blood samples, cerebrospinal fluid samples, synovial tissue samples, synovial fluid samples, brain tissue samples, blood vessel samples, or tumor (e.g., pituitary adenoma) samples.

The sample can be extracted to obtain FKBP1 protein, or FKBP5 nucleic acid. For example, cells can be lysed, and the protein fraction obtained. In some cases, the lysate is further fractionated to purify a specified cellular compartment. For example, the cell lysate can be fractionated to obtain a cytosolic protein fraction. As another example, the cell lysate can be fractionated to obtain a nuclear or nucleolar protein fraction. The protein fraction can be assayed for FKBP5 protein levels or activity. Alternatively, the cells can be lysed, and a nucleic acid (e.g., mRNA) fraction obtained. The nucleic acid fraction can be assayed for expression of the FKBP5 gene.

The cell lysate, or protein fraction thereof can be purified using a variety of methods to obtain a fraction enriched for FKBP5 protein, or a portion thereof. For example, cells can be lysed and contacted with a chromatography medium under conditions suitable to preferentially bind contaminants or target protein. Where contaminants are preferentially bound, target protein can be collected as a flow through fraction and assayed further. Where target protein is bound, the chromatography medium can be washed and the target protein eluted.

As another example, cells can be lysed and contacted with a capture reagent (e.g., a capture antibody or aptamer) that specifically binds to the FKBP5 protein, or a portion thereof. The capture reagent can be immobilized on a solid support. In some cases, the FKBP5 protein or portion thereof can be eluted from the capture reagent and then detected or quantified. In other cases, the FKBP5 protein or portion thereof can be detected or quantified as a capture reagent-bound form.

Similarly, the cell lysate, or nucleic acid fraction thereof can be purified using a variety of methods to obtain an fraction enriched for a transcript of a gene encoding FKBP5. For example, cells can be lysed and nucleic acids can be precipitated or otherwise purified from the lysate. In some cases, the nucleic acids can be purified by contacting the sample, or a fraction thereof, with a surface immobilized oligodT moiety to preferentially bind polyadenylated mRNA.

Nucleic acids can be subject to amplification, hybridization, polymerization, reverse transcription, or a combination thereof. In some cases, the amplification, hybridization, polymerization, or reverse transcription is target specific such that the gene encoding FKBP5, a transcript thereof, or a portion thereof is specifically amplified, hybridized, or reverse transcribed. In some cases, the amplification, hybridization, polymerization, or reverse transcription is not target specific such that the sample is subject to whole genome or whole transcriptome hybridization, polymerization, or reverse transcription. Whole genome or other non-specific hybridization, polymerization, or reverse transcription can be performed with the use of one or more degenerate primers or probes. After non-specific hybridization, polymerization, or reverse transcription, the FKBP5 gene expression can be specifically detected and/or quantified.

The amount or activity of FKBP5 polypeptide, or a portion thereof, can be measured by a variety of methods known in the art. For example, an ELISA (e.g., sandwich ELISA) can be used to measure polypeptide levels in a sample, or a protein extract thereof, using one or more antibodies specific for the FKBP5 protein, or a portion thereof. In some cases, the ELISA is a sandwich ELISA, in which FKBP5 polypeptide, or a portion thereof, is immobilized by binding to an immobilized capture reagent (e.g., capture antibody or aptamer), and the immobilized polypeptide or portion thereof is detected with a detection reagent (e.g., detection antibody or aptamer).

As another example, activity of the FKBP5 polypeptide, or a portion thereof, can be measured by contacting the sample, or a protein extract thereof, with a proline containing peptide substrate to measure the FKBP5-mediated cistrans prolyl isomerase activity of the sample. In some cases, the isomerization of the substrate can be measured using an cis-trans proline isomer sensitive enzyme, such as a protease. For example chymotrypsin, which has a high substrate specificity and catalytic efficiency ($k_{cat}$/Km) against peptide substrates having a trans-proline at the P2 position and phenylalanine or tyrosine at the P1 position, but very little or no specificity or catalytic efficiency against such peptides containing a cis-proline at P2, can be used to measure prolyl isomerase activity. For instance, an N-succinyl-Ala-Leu-cis-Pro-Phe-p-nitroanilide substrate can be used in combination with chymotrypsin, which preferably cleaves the trans prolyl isomer of the substrate to assay a sample or extract thereof for FKBP5 prolyl isomerase activity. The production of the trans isomer of the substrate by isomerase activity of the FKBP5 or portion thereof can be measured by detecting the digestion of the nitroanilide substrate by the chymotrypsin as described, e.g., in Fischer et al. Nature. 1989 Feb. 2; 337(6206):476-8.

As another example, activity of the FKBP5 polypeptide, or a portion thereof, can be detected or quantified by measuring the amount of FKBP5 protein bound to GR in the sample. This can be performed, e.g., by purifying GR or FKBP5 protein under conditions suitable to preserve binding between GR and FKBP5 protein. The purification product can then be assayed for the presence, absence, or quantity of the cognate binding partner. For example, cytosolic GR can be purified and the presence of FKBP5 protein detected in the purification product. As another example, FKBP5 protein can be purified and the presence of GR can be detected in the purification product. In some cases, this can be performed using a sandwich ELISA-type assay in which the immobilized capture reagent recognizes one member of the GR:FKBP5 protein complex and the detection reagent recognizes the other member of the GR:FKBP5 protein complex.

As another example, expression of a gene encoding FKBP5 protein can be measured by reverse transcription of FKBP5 mRNA, or a portion thereof, and quantitative amplification of the reverse transcription product or a portion thereof. The quantitative amplification can be performed using PCR (e.g., real time PCR) or other amplification techniques known in the art. The amplification can be detected by, e.g., detecting incorporation of an intercalating dye into the amplification product, degradation of a quenched fluorescence hydrolysis probe, or binding of quenched molecular beacon.

Any measured amount activity or expression level in a sample can be normalized to a reference. For example, expression level can be normalized to total mRNA levels, or the expression level of a reference gene. Suitable reference genes include, but are not limited to, GAPDH, hypoxanthine phosphoribosyltransferase 1 (HRPT1), ribosomal protein large P1, or another housekeeping gene. As another example, FKBP5 protein amount can be normalized to total protein levels, or the level of a reference gene product. Suitable reference gene products include, but are not limited to, actin, tubulin, COX IV, HRPT1, GAPDH, or another housekeeping gene product.

The amount or activity of FKBP5 protein or expression level of the gene encoding FKBP5 can be compared to a control value or threshold to indicate the presence or absence, or likelihood, of Cushing's syndrome. In some cases, the control or threshold is a positive control, such that when the amount or activity of FKBP5 protein or expression level of the gene encoding FKBP5 is near, equal to, or higher than the control or threshold value, Cushing's syndrome is indicated. In some cases, the control or threshold is a negative control, such that when the amount or activity of FKBP5 protein or expression level of the gene encoding FKBP5 is near, equal to, or below the threshold value, the absence of Cushing's syndrome is indicated.

EXAMPLES

I. Example I

Figure 2:
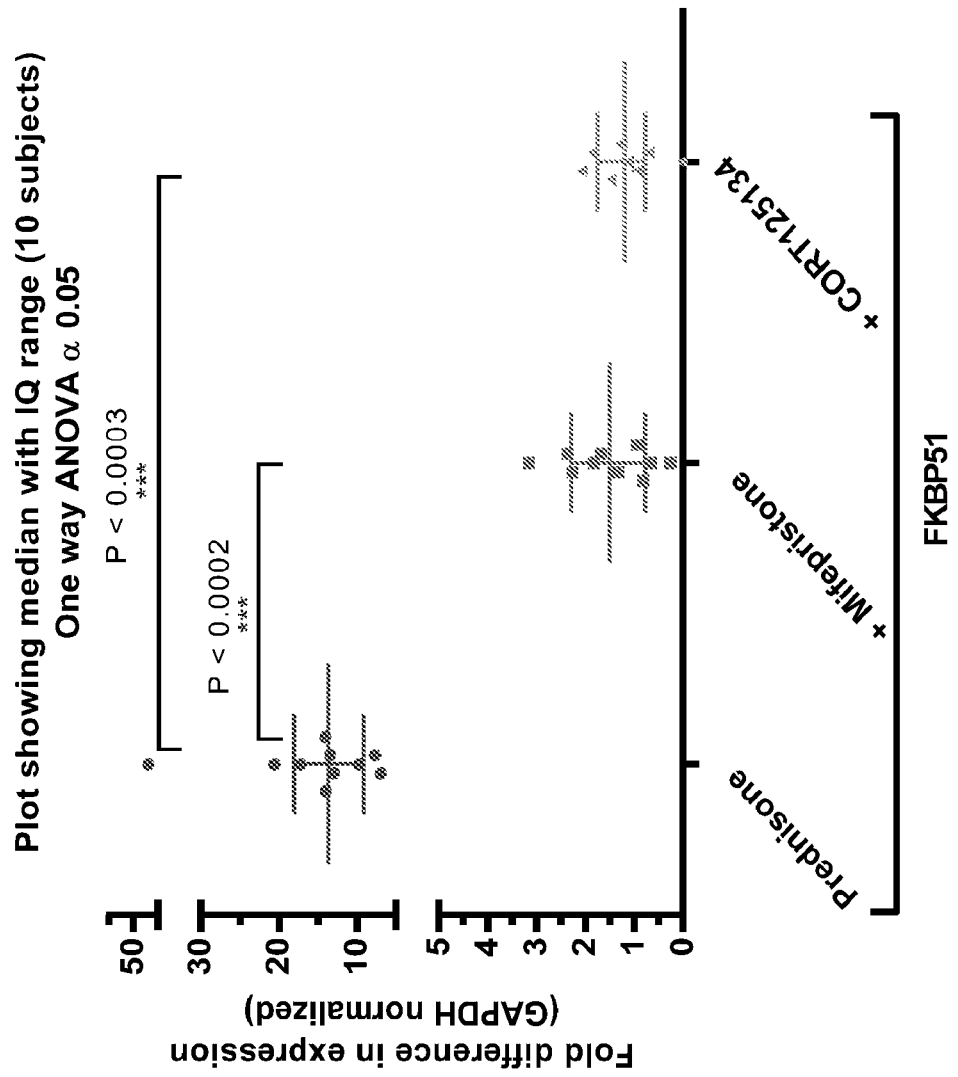
FIG. 2: depicts the fold difference in GAPDH normalized FKBP5 expression levels in samples taken before and after administration of the indicated GR agonist (prednisone), or before and after administration of the indicated GR agonist in combination with the indicated GR antagonist (mifepristone or CORT125134).

Ten healthy subjects are treated with prednisone on day −19. On day −12, subjects are treated with prednisone (25 mg) and mifepristone (600 mg). On day 1, subjects are treated with prednisone (25 mg) and CORT125134 (500 mg). Blood samples are taken before each dose and at various time-points after each dose. The study scheme is depicted in FIG. 1. The expression level of the FKBP5 gene is measured in the pre-administration samples obtained before dosing on each day and in the post-administration samples obtained at various time points after dosing on each day. Raw expression level data in the samples are normalized against the expression level of the glyceraldehyde phosphate dehydrogenase (GAPDH) gene in each sample. As illustrated in FIG. 2, the normalized expression level of the FKBP5 gene in the whole blood samples after administration of the GR agonist prednisone is from about 10 to 50 fold above the pre-administration level. Administration of the GRAs mifepristone or CORT125134 causes a significant decrease in the fold change in FKBP5 expression.

REFERENCES

Barik S. Immunophilins: for the love of proteins. Cellular and molecular life sciences: CMLS, 2006, 63:2889-2900.

Baughman G, Wiederrecht G. J, Campbell N F, Martin M M, Bourgeois S. FKBP51, a novel T-cell-specific immunophilin capable of calcineurin inhibition. Molec. Cell. Biol., 1995, 15: 4395-4402.

Binder E B, Salyakina D, Lichtner P, Wochnik G M, Ising M, Putz B, Papiol S, Seaman S, Lucae S, Kohli M A, Nickel T, Kunzel H E, Fuchs B, Majer M, Pfennig A, Kern N, Brunner J, Modell S, Baghai T, Deiml T, Zill P, Bondy B, Rupprecht R, Messer T, Kohnlein O, Dabitz H, Bruckl T, Muller N, Pfister H, Lieb R, Mueller J C, Lohmussaar E, Strom T M, Bettecken T, Meitinger T, Uhr M, Rein T, Holsboer F, Muller-Myhsok B. Polymorphisms in FKBP5 are associated with increased recurrence of depressive episodes and rapid response to antidepressant treatment. Nature genetics 2004, 36:1319-1325.

Binder E B, Bradley R G, Liu W, Epstein M P, Deveau T C, Mercer K B, Tang Y, Gillespie C F, Hein C M, Nemeroff C B, Schwartz A C, Cubells J F, Ressler K J. Association of FKBP5 polymorphisms and childhood abuse with risk of posttraumatic stress disorder symptoms in adults. JAMA, 2008, 299:1291-1305.

Binder E B. The role of FKBP5, a co-chaperone of the glucocorticoid receptor in the pathogenesis and therapy of affective and anxiety disorders. Psychoneuroendocrinology, 2009, 34(Supp. 1): S186-S195.

Blair L J, Nordhues B A, Hill S E, Scaglione K M, O'Leary J C 3$^{rd}$, Fontaine S N, Breydo L, Zhang B, Li P, Wang L, Colman C, Paulson H L, Muschol M, Uversky V N, Klengel, T, Binder E B, Kayed R, Golde T E, Berchtold N, Dickey C A. Accelerated neurodegeneration through chaperone-mediated oligomerization of tau. J. Clin. Invest. 2013, 123:4158-5169.

Caldwell J M, Blanchard C, Collins M H, Putman P E, Kaul A, Aceves S S, Bouska C A, Rothenberg M E. Glucocorticoid-regulated genes in eosinophilic esophagitis: a role for FKBP51. J. Allergy Clin. Immunol., 2010, 125:879-888.

Ewald R E, Wand G S, Seifuddin F, Yang X, Tamashiro K L, Potash J B, Zandi P, Lee R S. Alterations in DNA methylation of Fkbp5 as a determinant of blood-brain correlation of glucocorticoid exposure. Psychoneuroendocrinol. 2014, 44:112-122.

Kimura M, Nagai T, Matsushita R, Hashimoto A, Hirohata S. Role of FK506 binding protein 5 (FKBP5) in osteoblast differentiation. Mod. Rheumatol., 2013, 23:1133-1139.

Lee R S, Tamashiro K L, Yang X, Purcell R H, Harvey A, Wilbur V L, Huo Y, Rongione M, Wand G S, Potash J B. Chronic corticosterone exposure increases expression and decreases deoxyribonucleic acid methylation of Fkbp5 in mice. Endocrinol. 2010, 151:4332-4343.

O'Leary J C III, Zhang, B, Koren J III, Blair L, Dickey C A. The role of FKBP5 in mood disorders: Action of FKBP5 on steroid hormone receptors leads to questions about its evolutionary importance. CNS Neurol. Disord. Drug Targets, 2013, 12:1157-1162.

Pereira M J, Palming J, Svensson M K, Rizell M, Dalenback J, Hammare M, Fall T, Sidibeh C O, Svensson P-A, Eriksson J W. FKBP5 gene expression in human adipose tissue increases following dexamethasone exposure and is associated with insulin resistance, Metabolism, 2014, doi: 10.1016/j.metabol.2014.05.015.

Scammell J G, Denny W B, Valentine D L, Smith D F. Overexpression of the FK506-binding immunophilin FKBP51 is the common cause of glucocorticoid resistance in three New World primates. Gen. Comp. Endocrinol., 2001, 124:152-165.

Vermeer H, Hendriks-Stegeman B I, van der Burg B, van Buul-Offers S C, Jansen M. Glucocorticoid-induced increase in lymphocytic FKBP51 messenger ribonucleic acid expression: a potential biomarker for glucocorticoid sensitivity, potency, and bioavailability. J. Endocrinol. Metab. 2003, 88:277-284.

Wilbur V L, Chen H, Toolan J, Belmonte P, Cutler D J, Goes F S, Zandi P P, Lee R S, MacKinnon D F, Mondimore F M, Schweizer B, Bipolar disorder phenome group, NIMH genetics initiative bipolar disorder consortium, DePaulo J R Jr., Gershon E S, McMahon F J, Potash J B. Family-based association of FKBP5 in bipolar disorder. Mol. Psychiatry, 2009, 14:261-268.

Yang L, Isoda F, Yen K, Kleopoulos S P, Janssen W, Fan X, Mastaitis J, Dunn-Meynell A, Levis B, McCrimmon R, Sherwin R, Musatov, S, Mobbs, C V. Hypothalamic Fkbp51 induced by fasting, and elevated hypothalamic expression promotes obese phenotypes.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for diagnosing and treating hypercortisolemia in a human patient suspected of suffering from hypercortisolemia, said treatment comprising administration of a glucocorticoid receptor antagonist (GRA), the method comprising:

obtaining a difference value consisting of the average of at least 20 difference results obtained from a cohort of at least 20 individuals known to have or suspected of having Cushing's syndrome, said individuals not having been administered a GRA, by measuring the differences between a first and a second amount or activity of 51 kDa FK506 binding protein (FKBPS protein) or a first and a second expression level of a gene encoding FKBPS protein measured in first and second primary cell samples, respectively, where said first samples are obtained from each of at least 20 individuals prior to, and said a second samples are obtained from each of said individuals at least 2 hours after, administration of a GRA to each of the individuals, and subtracting the second measured amount, activity, or expression from the first measured amount, activity, or expression from that individual to obtain differences from which to derive said difference value;

wherein said difference value is termed a threshold difference value if the average of the second amount, activity, or expression is at least 15% less than the average of the first amount, activity, or expression;

Selecting a human patient suspected of suffering from hypercortisolemia but whose urinary free cortisol (UFC) test results are not abnormal, said patient not having been administered a GRA;

a) measuring a first amount, or activity of 51 kDa FK506 binding protein (FKBPS protein) or a first expression level of a gene encoding FKBP5 protein in a primary cell sample from said patient, said patient not having been administered a GRA, thereby obtaining a control value from the result of said measuring; then b) administering a GRA for treatment of hypercortisolemia to said patient; then c) measuring a second amount or activity of FKBP5 protein or a second expression level of a gene encoding FKBP5 protein in a second primary cell sample obtained from the patient after said GRA administration, wherein said second primary cell sample is obtained at least 2 hours after said GRA administration, thereby obtaining a response value from the result of said measuring; and d) subtracting said response value from said control value to obtain an FKBP5 difference value;

wherein an FKBP5 difference value that is equal to, or greater than the threshold difference value indicates a biochemical response to said GRA administration affecting cortisol activity in said cell samples from, and diagnoses hypercortisolemia in, the patient, whereby hypercortisolemia is diagnosed and a clinical response to said treatment of hypercortisolemia is detected in the patient, and the method comprises continuation of said GRA administration; and wherein, where the FKBP5 difference value is less than the threshold difference value, the method comprises administering no further medical treatment for hypercortisolemia to the patient.

2. The method of claim 1, wherein the GRA administered to the patient is mifepristone.

* * * * *

UNITED STATES PATENT AND TRADEMARK OFFICE
CERTIFICATE OF CORRECTION

| | |
|---|---|
| PATENT NO. | : 11,268,145 B2 |
| APPLICATION NO. | : 15/839666 |
| DATED | : March 8, 2022 |
| INVENTOR(S) | : Joseph K. Belanoff et al. |

It is certified that error appears in the above-identified patent and that said Letters Patent is hereby corrected as shown below:

In the Claims

Column 31, Line 42, Claim 1: delete "FKBPS" and insert --FKBP5--.

Column 31, Line 44, Claim 1: delete "FKBPS" and insert --FKBP5--.

Column 32, Line 15, Claim 1: delete "FKBPS" and insert --FKBP5--.

Signed and Sealed this
Twenty-first Day of March, 2023

Katherine Kelly Vidal
*Director of the United States Patent and Trademark Office*